US010087425B2

(12) United States Patent
Neidle et al.

(10) Patent No.: US 10,087,425 B2
(45) Date of Patent: Oct. 2, 2018

(54) CHIMERIC ENZYMES FOR CONVERSION OF LIGNIN-DERIVED CHEMICALS

(71) Applicants: Alliance for Sustainable Energy, LLC, Golden, CO (US); University of Georgia Research Foundation, Inc., Athens, GA (US)

(72) Inventors: Ellen Lee Neidle, Dacula, GA (US); Christopher W. Johnson, Denver, CO (US); Gregg Tyler Beckham, Golden, CO (US); Jeffrey G. Linger, Denver, CO (US); Mark Andrew Eiteman, Athens, GA (US); Melissa Tumen-Velasquez, Athens, GA (US); Alaa Ashraf Mahmoud Ahmed, Athens, GA (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/658,789

(22) Filed: Jul. 25, 2017

(65) Prior Publication Data
US 2018/0023061 A1 Jan. 25, 2018

Related U.S. Application Data

(60) Provisional application No. 62/532,611, filed on Jul. 14, 2017, provisional application No. 62/366,216, filed on Jul. 25, 2016.

(51) Int. Cl.
C12N 9/02 (2006.01)
C12P 7/44 (2006.01)
C12P 7/22 (2006.01)

(52) U.S. Cl.
CPC ......... *C12N 9/0069* (2013.01); *C12N 9/0071* (2013.01); *C12P 7/22* (2013.01); *C12P 7/44* (2013.01); *C12Y 113/11001* (2013.01); *C12Y 114/14001* (2013.01); *C07K 2319/00* (2013.01)

(58) Field of Classification Search
None
See application file for complete search history.

(56) References Cited

U.S. PATENT DOCUMENTS 4,952,501 A 4/1990 Jasin et al.
2016/0265006 A1 9/2016 Johnson et al.

OTHER PUBLICATIONS

Chica et al. Curr Opin Biotechnol. Aug. 2005;16(4):378-84.*
Singh et al. Curr Protein Pept Sci. 2017, 18, 1-11.*
Dammeyer et al. Microb Cell Fact. May 20, 2013;12:49.*
Diogo et al. Enzyme Microb Technol. Feb. 2015 Epub Dec. 5, 2014.*

Accession ADV69261. Mar. 10, 2005.*
Accession A0A076MY51. Oct. 29, 2014.*
Dardas et al., "The Demethylation of Guaiacol by a New Bacterial Cytochrome P-450", Archives of Biochemistry and Biophysics, Feb. 1985, vol. 236, No. 2, pp. 585-592.
Elliott et al., "*Acinetobacter baylyi* ADP1: Transforming the Choice of Model Organism", IUBMB Life, Dec. 2011, vol. 63, No. 12, pp. 1075-1080.
Elliott et al., "Copy Number Change: Evolving Views on Gene Amplification", Future Microbiology, 2013, vol. 8, No. 7, pp. 887-899.
Eltis et al., "Purification and characterization of cytochrome P450$_{RR1}$ from *Rhodococcus rhodochrous*", European Journal of Biochemistry / FEBS, 1993, vol. 213, No. 1, pp. 211-216.
Karlson et al., "Two Independently Regulated Cytochromes P-450 in a *Rhodoccus rhodochrous* Strain That Degrades 2-Ethoxyphenol and 4-Methoxybenzoate", Journal of Bacteriology, Mar. 1993, vol. 175, No. 5, pp. 1467-1474.
Kawahara et al., "Purification and Characterization of 2-ethoxyphenol-induced Cytochrome P450 from *Corynebacterium* sp. Strain EP1", Canadian Journal of Microbiology, 1999, vol. 45, No. 10, pp. 833-839.
Kim et al., "Physiological, Numerical and Molecular Characterization of alkyl ether-utilizing rhodococci", Environmental Microbiology, 2007, vol. 9, No. 6, pp. 1497-1510.
Nodate et al., "Functional Expression System for Cytochrome P450 Genes Using the Reductase Domain of Self-sufficient P450RhF from *Rhodococcus* sp. NCIMB 9784", Applied Genetics and Molecular Biotechnology, 2006, vol. 71, No. 4, pp. 455-462.
Patrauchan et al., "Catabolism of Benzoate and Phthalate in *Rhodococcus* sp. Strain RHA1: Redundancies and Convergence", Journal of Bacteriology, Jun. 2005, vol. 187, No. 12, pp. 4050-4063.
Sauret-Ignazi et al., "Purification and Properties of Cytochrome P-450 from *Moraxella* sp.", Biochimie, Oct. 1988, vol. 70, No. 10, pp. 1385-1395.
Seaton et al., "Genome-wide Selection for Increased Copy Number in *Acinetobacter baylyi* ADP1: Locus and Context-dependent Variation in Gene Amplification", Molecular Microbiology, 2012, vol. 83, No. 3, pp. 520-535.
Sterjiades et al., "Properties of a Bacterial Strain Able to Grow on Guaiacol", FEMS Microbiology Letters, May 1982, vol. 14, No. 1, pp. 57-60.
Studenik et al., "Characterization of an O-Demethylase of *Desulfitobacterium hafniense* DCB-2", Journal of Bacteriology, 2012, vol. 194, No. 13, pp. 3317-3326.
Sutherland, "Demethylation of Veratrole by Cytochrome P-450 in *Streptomyces setonii*", Applied and Environmental Microbiology, Jul. 1986, vol. 52, No. 1, pp. 98-100.

\* cited by examiner

*Primary Examiner* — Christian L Fronda
(74) *Attorney, Agent, or Firm* — John C. Stoloa; Alexandra M. Hall

(57) ABSTRACT

Disclosed herein are enzymes useful for the dealkylation of aromatic substrates, including the conversion of guaiacol or guaethol to catechol. Methods of converting aromatic substrates found in lignin-based feedstocks such as pyrolysis oil into products such as catechol are also disclosed. Also presented herein are methods for rapidly evolving and optimizing genetic regions.

18 Claims, 21 Drawing Sheets

Specification includes a Sequence Listing.

A – SEQ ID NO:1

ATGGAAGTTAAAATATTCAATACTCAGGATGTGCAAGATTTTTTACGTGTTGCAAGCGGACTTGAGCAAGAAGGTGGCAATCCGCGTGTAAAGCAGATCATCCATCGTGTGCTTTCAG
ATTTATAAAGCCATTGAAGATTTGAATATCACTTCAGATGAATACTGGGCAGGTGTGGCATATTTAAATCAGCTGGTGCCAATCAAGAAGCTGGTTACTTCTCGCCAGGTTGGG
TTTTGACCATTACCTGCGATATGCGTATGGATGATGGCAGCGATCCCGCACTAGTATGCCGAAGATGCCGACACACGTACCATTGAAGGCCCGCTATACGTGGCAGGTGCGCCTGAATCGGTA
GGTTATGCGCGATGGGATGACGGAAGTGATCAATTTGCCCCATATTCTATACCTGATTCTGCACGATCTTGATGCACGATGCGCCGTAGTATTATTACCGCCCGTAGTAACGGTTCAGTATTTGTTCTGCCGATGAACACCGCAAA
CCAATACCAAAGGCTTTATGGTTGCCCACCAGAAGGTCAACGCAACAGGCAGCAGCAGTTGCTGAATCAGTTGCCCTGCACACCTGCTTATGACGATTTGCTTATGACGACTTTGCTTATGACGACTTTGTTTCTGCCGATGAACACCGCAAA
CTAACTACGCAAATTAATGTGGCTGGCGATCCGTACGACCTATGACGACTTGCTTATGACGACTTTGCAACCGTGGCTTTGCTTATGACGACTTTGCAACCGTGGCTTTGCTTATGACGACTTTGATAAACCAaacgaacggcccgatctcgccctggctcgacgccgagtctgccgc
CCAATGATGTTGAAGGCCCATTCGCTGAAATGGTTTTCGATCTAAATTGACGCGTTTGATGGTGTAGATAACCAaacgaacggcccgatctcgccctggctcgacgccgagtctgccgc
gaagtcgcgaccagccgactcgagccgccgaggtgtacgaggtgtcatcacccccggctggcgtcaaccgcgatcatcggcgtcaagcgcgacatccacgcgacatcacgggcacgcgcctgcgttcaccaacgccgcc
tcgagccgccggtcagcgtcgagccgtccgcctcgggaggcttcagcgtcgatccgagcagcgccgagatctactacccggagtacgaaggccgagtccgccaccccgacg
gtcgagaacggcgagttcgccaaccccgaggccatgccaggcctggccgctgtggtcgagaacgcgagttcgccaaccccgaggccatgccaggcctggccgctgtggtcgacaaggtgatcgacaaggtgatcgacaaggtgatcgacaag
aagccattctgcactggctgcagacgacggccatgccgcccgtccaaccaggcggtgacctcggtctcctcgacgacgcggtgctcctacggccgaacccgcagcgcgagtacttcgacgtagtggcgatcgcaggaaccgccca
cggccatggccctccaacgtcgtgagtcgccaaccgcggacatcgcgagtcgccaacccgacgacgccgtgcgcccaaccaggtcgccaaccgcggggtcgctcgcccaaccgtcctgaatctgaccgtcggtggcggcgttcgccctcggaccttcgcatgcctcagcgatcgcgaaccgtccaaccaccggtcctgcaacagcggcgatcatgcggcct
acgaggcccctgagtacgacgcctcgaccgtccgagtcgcagtgcccctcggcgaccagccggggcaaccaggtgcgcaacggccctgtaccttcgcaaccatcttcgccaaccacgtcctacttcgccaaccacgtccgtccgacttccgcgctgcggccaccggatcgcgct
ggaggagctgttcgaggtcgagtggggcttccgcggtctgggggctcgagttctcgagggcgtcgagttctgagggcgtcgagttctcgagggcgtcgagttctgcaccctccgcacgtcacctgggaggtg

B – SEQ ID NO:2

MEVKIFNTQDVQDFLRVASGLEQEGGNPRVKQIIHRVLSDLYKAIEDLNITSDEYWAGVAYLNQLGANQEAGLLSPGLGFDHYLDMRMDARDAALGIENATPRTIEGPLYVAGAPES
VGYARMDDGSDPNGHTLLHGTIFDADGKPLPNAKVEIWHANTKGFYSHFDPTGEQQAFNMRRSIITDENGQYRVRTILPAGYGCPPEGPTQQLLNQLGRHGNRPAHIHYFVSADGH
RKLTTQINVAGDPYTYDDPFAYATREGLVVDAVEHTDPEAIKANDVEGPFAEMVFDLKLTRLVDGVDNQTERPDLAWLDEVTMTQLERNPYEVYERLRAEAPLAFVPVLGSYVASTAE
VCREVATSPDFEAVITPAGGRTFGHPAIIGVNGDIHADLRSMVEPALQPAEVDRWIDDLVRPIARRYLERFENDGHAELVAQYCEPVSVRSLGDLLGLQEVDSDKLREWFAKLNRSF
TNAAVDENGEFANPEGFAEGDQAKAEIRAVVDPLIDKWIEHPDDSAISHWLHDGMPPGQTRDREYIYPTIVYLLGAMQEPGHGMASTLVGLFSRPEQLEEVVDDPTLIPRAIAEGL
RWTSPIWSATARISTKPVTIAGVDLPAGTPVMLSYGSANHDTGKYEAPSQYDLHRPPLPHLAFGAGNHACAGIYFANHVMRIALEELFEAIPNLERDTREGVEFWGWGFRGPTSLHV
TWEV

FIG. 1

A — SEQ ID NO:3 atgacgacgacgaaccggcccgatctcgcctggctcgacgaggtcaccatgacgcagctccgagcgaaccccgtacgaggtgtacgagcggctgcgcgaggcggctgcgcttcg
tgccggtgctgggtcctacggccacatcggcctcgacgtcgccgaagtcgtgcccgaccagccgcgacctgcaacgtcctcgaggccgtcatcaaccccgaccttcgaggccgtcaatccggagcgtgcgcgtcgggcaccccgagc
gatcatcggcgtcaacgcgcacatccacgccgacatccgcgctccatgtcgcgcagtactgcgagtcgcgcgtggcgcagtactgcgagcccggtcagcgtcgcctcggcctgtcgaggaggtcgactcgacaagc
tacctggagcggttcgaaaacgacggcacgcgcaactgcgaactggttcaccacgagcgcgcgaactgcgagtcgcggagcggaacggcgagttcgccaaccgagggcttcgcgcccgagggcgaccaggcaggccgagtacctac
tgcgcgagtgtctgaccggtggtctgaccgggccgtgttcaaccacgagcgccgtgatcgagaactggatgcgcaggagccacccggccacgccatgcgcgcgcatgccaggccgtttcaggcgcggatgctcagcaaaagcggctgcaccaaagccgtggatgtgccgccccggac
ccgacatctacgtgctcggcgagatgctgcggccgatgcgcaggaaccccggccacgcccggcgggcctgcaacgaccacggcgcaacacacaggcgcagtacgacacaagacgggtgaccatcagaccccggacgtgcaccgggtcgacctgccggcgaccac
gccggtgatgctctcctacggctcggccaaccacgcatgcggatcgcgctggaaggtgttccaggaagctcgagcgtgttggagcgggtttgaggccaaccccgaaccctggagcgcgacaccccgagcgcgagcgggtcgagttcctgggggctggg
gcttccgcggccccaccctcgctgcacgtcacctgggaggtg

B — SEQ ID NO:4

MTTTERPDLAWLDEVTMTQLERNPYEVYERLRAEAPLAFVPVLGSYVASTAEVCREVATSPDFEAVITPAGGRTFGHPAIIGVNGDIHADLRSMVEPALQPAEVDRWIDDLVRPIAR
RYLERFENDGHAELVAQYCEPVSVRSLGDLLGLQEVDSDKLREWFAKLNRSFTNAAVDENGEFANPEGFAEGDQAKAEIRAVVDPLIDKWIEHPDDSAISHWLHDGMPPGQTRDREY
IYPTIYVYLLGAMQEPGHGMASTLVGLFSRPEQLEEVVDDPTLIPRAIAEGLRWTSPIWSATARISTKPVTIAGVDLPAGTPVMLSYGSANHDTGKYEAPSQYDLHRPLPHLAFGA
GNHACAGIYFANHVMRIALEERLFEAIPNLERDTREGVRFWGWGFRGPTSLHVTWEV

FIG. 2

A – SEQ ID NO:5

ATGGAAGTTAAAATATTCAATACTCAGGATGTGCAAGATTTTTTACGTGTTGCAAGCGGACTTGAGCAAGAAGGTGGCAATCCGCGTGTAAAGCAGATCATCCATCGTGTGCTTTCAG
ATTTATAAAAGCCATTGAAGATTTGAATATCACTTCAGATGAATATTGGGCAGGTGTGGCATATTAAATCAGCTAGGTGCCAATCAAGAAGCTGGTTTACTCTCGCCAGGCTTGGG
TTTTGACCATTACCTCGATATGCTATGATGCCGACACACCTGAAGATGCCGCACTAGGTATTGAAAATGCGACACCACTTGAAGGCCTATACGTGGCAGGTGCGCCTGAATCGGTA
GGTTATGCGCATGGATGACGGAAGTGATCGAAATCACTTCGAAATGGTCATACCCTGATTCTACATGGCACGATCTTTGATGCAGATGGAAAACCTTTACCAATGCAAAGTTGAAATCGGCATG
CCAATACCAAAGGCTTTATTCACACTTCGACCCAACAGGCGAGCAGCAGTCGAATCAGTTGCTGAATCAGTTGCGTCATGGGCCGTCATGGGCCGTTCAATACCGGTCATATGCGCGTTCGTACCATTTTGCC
TGCGGGGTTATGGTTGCCCACCAGAAGTCCAACGTCGATCGGCGTACACCTATGACGACTTTGCTTATGCAACCCGTGGTGCAGGCTTGGTTGGTCAGTGGAACACACCGATCCTGAAGCATTAAGG
CTAACTACGCAAATTAATGTGCTGAAGCCCATTCGCTGAAATGGTTTCGATCTAAAATTGACGCGTTTGGTTGATGGTGTAGATAACCAAGTTGTTGATCGTCCACGTCTAGCGGTG
CCAATGATGTTGAAGGCCCATTCGCTGAAATG

B – SEQ ID NO:6

MEVKIFNTQDVQDFLRVASGLEQEGGNPRVKQIIHRVLSDLYKAIEDLNITSDEYWAGVAYLNQLGANQEAGLLSPGLIGFDHYLDMRMDAEDAALGIENATPRTIEGPLYVAGAPES
VGYARMDDGSDPNGHTLILHGTIFDADGKPLPNAKVEIWHANTKGFYSHFDPTGEQQAFNMRRSIITDENGQYRVRTILPAGYGCPPEGPTQQLLNQLGRHGNRPAHIHYPVSADGH
RKLTTQINVAGDPYTYDDFAYATREGLVVDAVEHTDPEAIKANDVEGPFAEMVFDLKLTRLVDGVDNQVVDRPRLAV

FIG. 3

A – SEQ ID NO:7

GTGACGTTCGCGGTCAGCGTCGGGGGCAGGCGGTCGACTGCGAGCCCGGCGTTCCTGCTGGAGGCGTTCCTGCGCGGCGGGGTGTGGATGCCCAACTCGTGCAACCAGGGCACCT
GCGGCACCTGCAAGCTGCAAGTCCTCAGCGGTGCTCTCCGGCGAGGTCGACCACGGCGCCCCCGGAGGACACCCTCAGCGCCGTCCGGGACTGGCGCTCGCCTGCCAGGCCCGTCC
GCTGCCCGACACGGAGGTGCCAGCGCCCGGGCGCAGTACGTCGAGCTGGTCGTGTCCCGGCTCGAGCTGCCCAGTACTCGCTGGCCAACACGGGCCGAGGACAAGG
CTGCTGGGCCTGCGAGCCCGGCTGGCGCGTTCCCGGTGGGGTCGCCACGGCCCGGGGTCGCCGTGCCACCCGACGGGGCTCGAGGCGACCGGGCCTGCCACCCGTCGCCGAAGTG
TGCTGGAGCTGCACGTGCCGACGAGGACGACGGGCGGCGCGATGGTGCTGCCGATCGGCGGGAACCTGGGCCGCGATCGCCCCGGTTCCGGCACCCGGTCTGCCGGTCGACGAGCCGGATC
GCCGCCGGACCGGGGCGGTTCCCGACCAGCGCGTTCGTCGACACGTCCCAGTGGACGCGTGGTCCGGCGCTGGTCCCCGCCGATGGTCGAGGCCCGGGGTGAAGGCGTT
CGGCGTACCGGGGCGGTTCCCGACCAGCGCGTTCGTCGAGGACGAAGTTCACGCCGGCCTCG

B – SEQ ID NO:8

MTFAVSVGGRRVDCEPGQTLLEAFLRGGVWMPNSCNQGTCGTCKLQVLSGEVDHGGAPEDTLSAEERASGLALACQARPLADTEVRSTADAGRVTHPLRDLTATVLEVADIARDTRR
VLLGLAEPLAFEAGQYVELVVPGSGARRQYSLANTADEDKVLELHVRRVPGGVATDGWLFDGLAAGDRVEATGPLGDFHLPPDEDDGGPMVLIGGGTGLAPLVGIARTALARHPSR
EVLLYHGVRGAADLYDLGRFAEIAEEHPGRFRFVPVLSDEPDPAYRGGFPTDAFVEDVPSGRGWNSGWLCGPPAMVEAGVKAFKRRRMSPRRIHREKFTPAS

FIG. 4

A – SEQ ID NO: 9

ATGGAAGTTAAAATATTCAATACTCAGGATGTGCAAGATTTTTTACGTGTGTTGCAAGCGGACTTGAGCAGGAAGGGTGGCAATCCGCGTGTGTAAAGCAGATCATCATCGTGTGCTTCAG
ATTTATATAAGCCATTGAAGATTTGATATCCAGATGAATCACTTCGATATGCGATAATGGGACTGCAAGCTGGTGCCATCAGCTACCATTGAAGACAACATCAGCTACCATGGTCTCGCCAGGCTTGGG
TTTTGACCATTACCTTGCGATATGCTATTGAATGAGCCGCACTAGGTATTCTACATGGCACGATCTTTGATGCAGATGGAAAAACCTTTACCCAATGCTATACGTGGCAGGTGCCTGAATCGTA
GGTTATGCGCGCATGGATGACGAAGTGATCCAAATGGTCATTCAGCGAGCAGGACTTGATCCAGAACTCAGATCTCAAATCGCGTTCGTACCATTTGCC
CCAATACCCAAAGGCTTTTATTCACCACCAGAAGTCTGACCAGCAACAGTTGCTGAACTTGCTGACGACTTTGGTCGATATGCCATGGAACCGTGAGTCGGATATCGGCACACCGAAGACCGCAAA
CTAACTACGCAAATTAAGGCCCCATTGGTGGCGATCCGTACACTTCGATCTAAAATTGGTTTCGATCTATAATTATAATCATGTGAAGACCCGTGAGGAGGAAGGACAGCTatgacgaccggaaccggccgatctcgcctggctcgac
gaggtcaccatgacgcagctcgagcgcaaccgtcgaggtgtacgagggcgtgcgcgtggagggcgtggcctttcgtcgccagaccctgcgacgatatcatcggcgtcacgcgacatcgcggctgcg
tctgccagtcgagcgcgaggggcgcgaggggcgggacctttggggcacggccgacctggttgcggcgtccaagcgcggcgctgacggcgactg
gtggcagtactcgagacgctgagcggtcagcgcagctcggcgaggtgtcaagggaacctgctacaccccgagatcctaccaccccgagagctgagctgacgacgaggaggaagcagtg
acgcgcgacagccgccatttcgcactggctccaccctgttcagcaggcccagcagctgaagaggtgtgcgacgaccgcgcgcgaggccgagggctgcggatgac
gcgcacgacggccatgctcctccaccgccgctccatcctcccccttccaagcaggtgcccggcgatcctcactcgcggccaaacacgcacac
cggcaggtacgagcggcagccgccctccagtagctacgacctgccagcgaggctgagctcctcagctgctcgacgacgtagcccaaccacgacgacac
atcggctggaggagctgttcgaggccatcccagccggcagtgcgagttcgccgggctcgggtcccgagatcctcggccccaagcgcggcc
tg

B – SEQ ID NO: 10

MEVKIFNTQDVQDFLRVVLQADLSRKGWQSAIPRVWCLTKQIHRVLSDLYKAIEDLNITSDEYWAGVAYLNQLGANQEAGLLSPGLGFDHYLDMRMDAEDALGIENATPRTIEGPLYVAGAPES
VGYARMDGSDPNGHTLILHGTIPDADGKPLPNAKVEIWHANTKGFYSHFDPTGEQQAFNMRRSIITDENGQYRVRTILPAGYGCPPEGPTQQLLNQLGRHGNRPAHIHYFVSADGH
RKLTTQINVAGDPYTYDDFAYATREGLVVDGVDNQVVDRPLARLVRLMQFACDPTITVIGKYNHGKSRLERRTAMTTTERPDLA
WLDEVTMTQLERNPYEVYERLRAEAPLAFVPVLGSYVASTAEVCREVATSPDFEAVITPAGGRTFGHPAIIGVNGDIHADLRSMVEFALQPAEVDRMLDDLVRPIARRYLERFENDG
HAELVAQYCEPVSVRSLGDLLGLQEVDSDKLREWFAKLNRSFTNAAVDENGEFANPEGFAEGDQAKAEIRAVVDPLIDKWIEHPDDSAISHWLHDGMPPGQTRDREYIYPTIVYLL
GAMQEPGHMASTLVGLFSRPEQLEEVVDDFTLIPRAIAEGLRWTSPIWSATARIISTKPVTIAGVDLPAGTPVMLSYGSANHDTGKYEAPSQYDLHRPLPHLAFGAGNHACAGIYF
ANHVMRIALEELPEAIPNLERDTREGVEFWGWGFRGPTSLHVTWEV

FIG. 18

A – SEQ ID NO: 11 atgacgacgacgaacggccgatctcgctggctcgacgaggtcaccatgacgcagctcgagcgtacgaggtgtacgagcggtgcgcgcgaggcgccgctgcct
tcgtgccggtggtggggtcgtcaactgcgcctcgacgccgaagtctgcgcggacgcccagccgcagctcgaccacttcgaggcgcgcgacttcgaggcga
ccgcggatcaatcggcgtcaacgccgacatccacgcggtctgctgcgtccatgtggcggcgaactgcgaaacgacgggcgaactcgaggcgcgtcgag
gcgcgcctacctgagcggttcgaaaacgacgggtgcgccaactgcgcgaacgcgtcgttcaccaacgacgacaacgcgcgagtccgaacgcgcgagagtcg
actcggacaagctgcgcgagctgtcgtgtcgacgatctacgtgtcggcgacccaacccgctgcgacacgaacgggagctctcgactgcgtcgactgcgactcggagcgcactccacccctgcctccaacctgtcggcgcatctccaccaagcgtgaccatcgc
cgggtctgacctgcgaccgcgcacgcggcacccgggacctgcgccaaccacgacaccgtcatgcggatcgcgctggaggagcgtgttcgaggcgactcccgaacctgagcgcgaca
cactcgcctggcgggctcggggctcccgcggcccaacctgctgcacgtcacctgggaggtg

B – SEQ ID NO: 12

MTTTERPDLAWLDEVTMTQLERNPYEVYERLRAEAPLAFVPVLGSYVASTAEVCREVATSPDFEAVITPAGDRTFGHPAIIGVNGDIHADLRSMVEPALQPAEVDRWIDDLVRPIAR
RYLERFENDGHAELVAQYCEPVSVRSLGDLLGLQEVDSDKLREWFAKLNRSFTNAAVDENGEFANPEGFAEGDQAKAEIRAVVDPLIDKWIEHPDDSAISHWLHDGMPPGQTRDREY
IYPTIYVLLGAMQEPGHGMASTLVGLFSRPEQLEEVVDDPTLIPRAIAEGLRWTSPIWSATARISTKPVTIAGVDLPAGTPVMLSYGSANHDTGKYEAPSQYDLHRPPLPHLAFGA
GNHACAGIYFANHVMRIALEELFEAIPNLERDTREGVEFWGWGFRGFPTSLHVTWEV

FIG. 19

A – SEQ ID NO:13

GTGACGTTCACGGTCAGCTCGGGGGACGTCGGGGGACAGGCGGTCGACTGCGAGCCGGGTCGGGGGTGTTCCTGCGGCGGCGGGTGTGTGGATGCCGAGCCCAACTCGTGCAACCAGGGCACCT
GCGGCACCTGCAAGCTCCAGGTGCTCTCCGGCGAGGTCGACCACGGAGCAGGAACACCCTCGAGGAGACACCCGACCTTGGGGACTGGCTCTTCGACGGGGTGGCGACGGACGGATGGCTGTTCGACGGCGTCCC
GCTCGCCGACACGGAGGTGCCGCAGCAGCCTGGCGTTCGCTGGAGCCGTGACCGTGACCGTGACCGTGACCATCGCGCGGGACATCCGCGCTCGAGGTCGCCGACATCGCGCCACCCCGGGGTG
CTGCTGGGAGCCTGGCGCGCGTCCCGGAGCGGTTTCGAGGCCGCGGCGACTACGTCGAGCTGGTCCTGTGCCGCCAGGCAGTACTCGTCGAGCCCGGCCAACACGGCCGCTCGGCGACTTCCACCT
TGCCGGAGCTGCAGTCGACGTCCCGGACGAGGACGAGGAGGACGAGGAACGGCCGGGCCGGTCGGGGTCTCTTCGACGGGCTCGAGGGCGACCGGGCGATCCGCCCGGCACCCCCGTCGCCGAAGTG
GCCGCCGCCGGACGCGGCCGCGGCGCTGGTGGTCCGGGCCGATCTCCGGCGGGGAAACCTGGGCTGGAAACTGGGCTGCCCGAAGATCCGCGAGCGTGCGCCTGGCCGCCTTCGTGCCGCGGCCGATCGGGGCCGGATC
CTGCTGTACCACGGGGTGCGCGCGCGCGACGCCCGGTTCGCAGGAGCGCCGGTTCGCCAGTCCGGGCGACCTGGCGTCCCCAGTGGACGCGGCTCGTGCCGGCTGCTGTGCGGCCCCGGCCGATGGGTCGAGGCCGGGGGTCGAAGGCCGTT
CGGGTACCGGGCGGTTTCGCCCGACGACGCGTTCGTCGAGGACGAGGTTCACCGGGAGAAGTTCACGCCGGCCTCG
CAAACGGGCGGCCATGTGCGCCGCGGCGGATCCACCCGGGAGAAGTTCACGCCGGCCCTCG

B – SEQ ID NO:14

MTFIVSVGGRRVDCEPGQTLLEAFLRGGVWMPNSCNQGTCGTCKLQVLSGEVDHGGAPEDTLSAEERASGLALACQARPLADTEVRSTADAGRVTHPLRDLTATVLEVADIARDTRR
VLLGLAEPLAFEAGQYVELVVPGSGARRQYSLANTADEDKVLELHVRRVPGGVATDGWLFDGLAAGDRVEATGPLGDFHLPPPDEDDGGPMVLIGGGTGLAPLVGIARTALARHPSR
EVLLYHGVRGAADLIYDLGRFAEIAEEHPGFRFRFVPVLSDEPDPAYRGFPTDAFVEDVPSGRGWSGWLCGPPAMVEAGVKAFKRRMSPRRIHREKFTPAS

FIG. 20

CHIMERIC ENZYMES FOR CONVERSION OF LIGNIN-DERIVED CHEMICALS

CROSS-REFERENCE TO RELATED APPLICATIONS

This application claims priority to U.S. Provisional Application No. 62/366,216, filed Jul. 25, 2016, and U.S. Provisional Application No. 62/532,611, filed Jul. 14, 2017. The contents of each application are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "16-21_ST25.txt," having a size in bytes of 75 kb and created on Jul. 25, 2017. Pursuant to 37 CFR § 1.52(e)(5), the information contained in the above electronic file is hereby incorporated by reference in its entirety.

BACKGROUND

Lignocellulosic biomass represents a vast resource for the production of renewable transportation fuels and chemicals to offset and replace current fossil fuel usage. The lignin component of lignocellulosic biomass is an energy-dense, heterogeneous alkyl-aromatic polymer comprised of phenylpropanoid monomers used by plants for water transport and defense, and it is the second most abundant biopolymer on Earth after cellulose. Lignin is typically underutilized in most selective conversion processes for biofuel production. In the production of fuels and chemicals from biomass, lignin is typically burned for process heat because its inherent heterogeneity and recalcitrance make it difficult to selectively upgrade the monomers to value added products. This limited ability to utilize lignin, despite being the most energy dense polymer in the plant cell wall, is primarily due to its inherent heterogeneity and recalcitrance. Guaiacol (2-methoxyphenol) is one of many products that result from lignin depolymerization.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide isolated DNA molecules encoding chimeric enzymes comprising a cytochrome P450 polypeptide and a catechol 1,2-dioxygenase polypeptide.

In various embodiments, the chimeric enzymes comprise at least 90% of the amino acids of the cytochrome P450 polypeptide GcoA from *Amycolatopsis* sp. ATCC 39116 and/or at least 90% of the amino acids of the catechol 1,2-dioxygenase CatA from *Acinetobacter baylyi* ADP1.

In some embodiments, the chimeric enzymes have amino acid sequences at least 90% identical to SEQ ID NO:2 or SEQ ID NO:10 or the amino acid sequences of SEQ ID NO:2 or SEQ ID NO:10.

In other embodiments, the isolated DNA molecules have an exogenous promoter operably linked to the DNA molecule. Also included are expression vectors comprising the DNA molecules and enzyme polypeptides encoded by the DNA molecules.

Additional embodiments provide host cells that express recombinant polypeptides encoded by the DNA molecules. The cells may be from a strain of *Pseudomonas* or *Acinetobacter*, such as *P. putida*.

Further embodiments provide methods for removing an alkyl group from an aromatic substrate or aromatic substrate containing material by contacting a material containing the aromatic substrate with a chimeric enzyme (including an enzyme comprising a cytochrome P450 polypeptide and a catechol 1,2-dioxygenase polypeptide) to generate a dealkylation product.

In some embodiments, the contacting step comprises culturing a microorganism expressing the chimeric enzyme with the material containing the aromatic substrate.

In various embodiments, the aromatic substrate comprises guaiacol, catechol, anisole or guaethol or the material containing the aromatic substrate comprises products of lignin depolymerization, pyrolysis oil or bio-oil.

In certain embodiments, the dealkylation product is catechol, phenol or cis,cis-muconic acid. Further embodiments may also include a step of isolating the dealkylation product.

Also provided are DNA molecules encoding point mutants of the enzymes disclosed herein and use in the disclosed methods.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleic acid sequence (A) and amino acid sequence (B) of a chimeric enzyme created by fusing the catechol 1,2-dioxygenase CatA from *Acinetobacter baylyi* ADP1 (underlined) and the cytochrome P450 O-dealkylase GcoA from *Amycolatopsis* sp. ATCC 39116.

FIG. 2 shows the nucleic acid sequence (A) and amino acid sequence (B) of the cytochrome P450 O-dealkylase GcoA from *Amycolatopsis* sp. ATCC 39116.

FIG. 3 shows the nucleic acid sequence (A) and amino acid sequence (B) of the catechol 1,2-dioxygenase CatA from *Acinetobacter baylyi* ADP1.

FIG. 4 shows the nucleic acid sequence (A) and amino acid sequence (B) of the reductase GcoB from *Amycolatopsis* sp. ATCC 39116.

FIG. 18 shows the nucleic acid sequence (A) and amino acid sequence (B) of a chimeric enzyme created by fusing the catechol 1,2-dioxygenase CatA (underlined), and part of the ACIAD1443 (orf1)-encoded protein from *Acinetobacter baylyi* ADP1 (double underlined) and the cytochrome P450 O-dealkylase GcoA from *Amycolatopsis* sp. ATCC 39116 (neither bold nor underlined).

FIG. 19 shows the nucleic acid sequence (A) and amino acid sequence (B) of the G72D variant cytochrome P450 O-dealkylase GcoA. The nucleotide change G215A and the amino acid change is G72D are underlined.

FIG. 20 shows the nucleic acid sequence (A) and amino acid sequence (B) of an A4T variant GcoB. The nucleotide change G10A and the amino acid change is A4T are underlined.

DETAILED DESCRIPTION

Disclosed herein are enzymes, organisms expressing these enzymes, and methods useful for the dealkylation of aromatic substrates, including the conversion of guaiacol or guaethol to catechol (and subsequently the conversion of catechol to cis,cis-muconic acid) or the conversion of anisole to phenol. The enzymes may exhibit increased expression levels or increased activity to one or more substrates as compared to wild-type enzymes. Methods of converting aromatic substrates found in lignin-based feedstocks such as pyrolysis oil into catechol, phenol or cis,cis-muconic acid are also disclosed. Also presented herein are methods for rapidly evolving and optimizing genetic regions.

Guaiacol (2-methoxyphenol), anisole (methoxybenzene), and guaethol (2-ethoxyphenol) are common products of lignin depolymerization, and the conversion of guaiacol or guaethol to catechol (1,2-dihydroxybenzene) allows the more efficient use of products derived from lignin. Catechol 1,2-dioxygenases are ring-cleavage dioxygenases with the ability to enzymatically convert catechol to cis,cis-muconic acid.

In certain embodiments, the enzyme may be a fusion between a catechol 1,2-dioxygenase and a cytochrome P450 O-dealkylase, or fragments of each enzyme containing the catalytic activity of each enzyme. FIG. 1 presents the nucleic acid sequence and amino acid sequence of an exemplary fusion enzyme useful for the enzymatic conversions described herein. In this example, the catechol 1,2-dioxygenase CatA from *Acinetobacter baylyi* ADP1 is fused to the cytochrome P450 O-dealkylase GcoA from *Amycolatopsis* sp. ATCC 39116.

The complete nucleic acid sequences and amino acid sequences for the cytochrome P450 O-dealkylase GcoA from *Amycolatopsis* sp. ATCC 39116 and the catechol 1,2-dioxygenase CatA from *Acinetobacter baylyi* ADP1 are presented in FIGS. 2 and 3, respectively. In the specific fusion of these proteins presented in FIG. 1, the nucleic acids encoding the CatA portion are in uppercase and underlined while those encoding the GcoA portion are in lowercase in Panel A. In Panel B of FIG. 1, the amino acids of the CatA portion are underlined while those encoding the GcoA portion are not underlined. In this exemplary embodiment, the first nine amino acids on the C-terminus of CatA are deleted, while the first three amino acids on the N-terminus of GcoA are also deleted.

Figure 10:
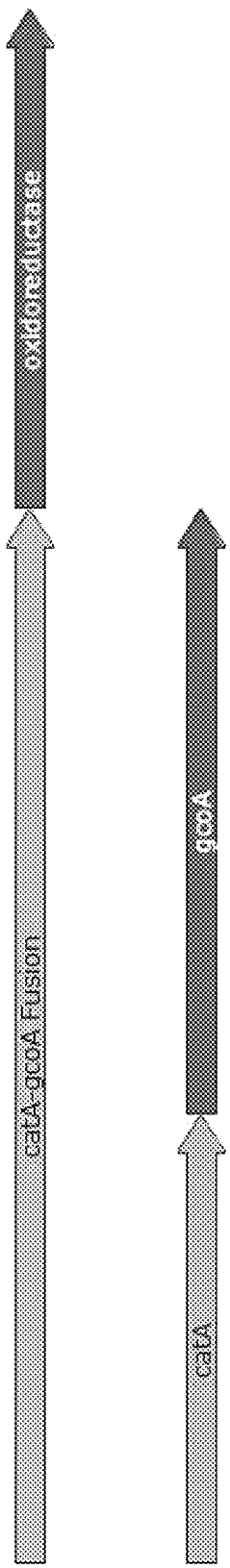
FIG. 10 shows a diagram of the catA-gcoA fusion (ACN1738).

In one embodiment, the CatA-GcoA fusion construct includes the nucleotides encoding CatA and GcoA but with the deletion last 30 bp of CatA and the first 9 bp of gcoA. The resulting fusion protein thus excludes the C-terminal 10 amino acids of CatA and the N-terminal 3 amino acids of GcoA. This embodiment is depicted in FIGS. 1 and 10 and in SEQ ID NOS: 1 and 2. The nucleotides encoding this fusion were captured on plasmid pBAC1314 by gap repair method, which was linearized and used to transform wild-type ADP1. The resulting mutant strain was designated ACN1739 and was capable of growth with guaiacol as the sole carbon source (guaiacol+). Subsequent analysis confirmed ACN1739 possesses a single copy of the fusion construct.

Figure 11:
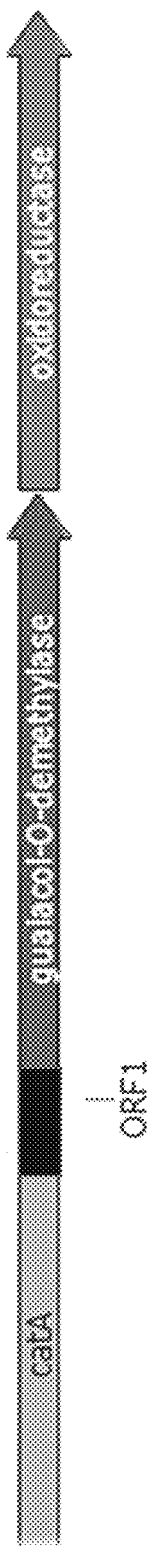
FIG. 11 shows a diagram of the catA-ORF1-gcoA fusion (ACN1764).
Figure 12:
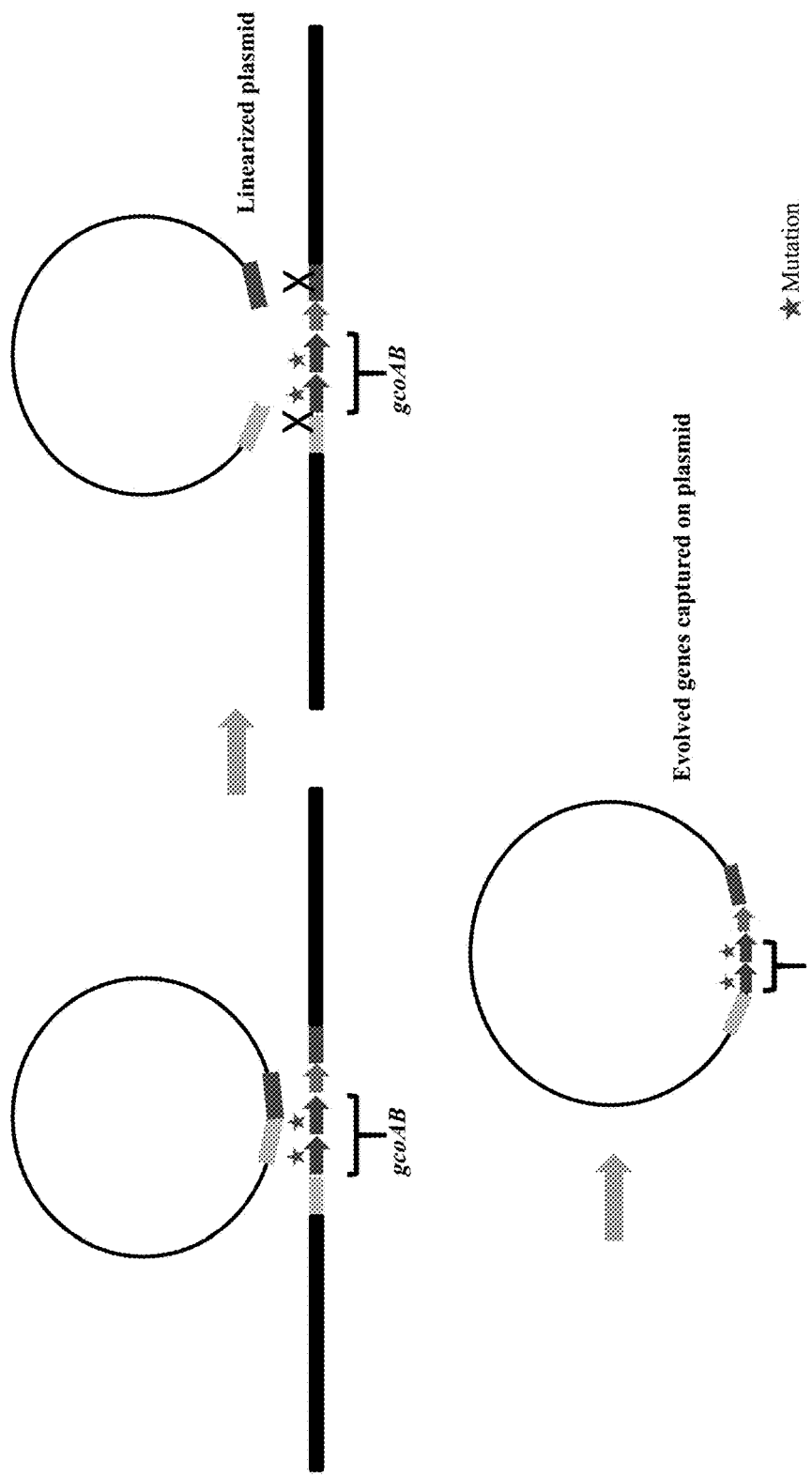
FIG. 12 show diagrams of the gap repair method.

In additional exemplary embodiments, the CatA-GcoA fusion construct may also include an intervening orf1 (ACIAD1433) coding sequence. One example of this construct is set forth in FIGS. 11 and 18 and in SEQ ID NOS: 9 and 10. In this exemplary fusion construct, the last 14 bp of the nucleotides encoding CatA (including the stop codon) are deleted, 9 bp between the catA and orf1 (ACIAD1433) coding sequences are also deleted, along the first 145 bp of orf1. This deletion places catA-orf1 and a short synthetic DNA piece with a ribosome binding site (RBS) in-frame with the entire gcoA coding sequence. In the resulting fusion protein, the last four amino acids of CatA (RLAV) are removed, and a linker peptide tethers CatA and GcoA. This tether consists of 29 amino acids encoded by Orf1 and 5 amino acids encoded by the inserted RBS DNA segment (ERRTA). The nucleotides encoding this fusion were captured on plasmid pBAC1337 by gap repair method, which was linearized and used to transform wild-type ADP1. The resulting mutant strain was designated ACN1762 and was guaiacol+. Subsequent analysis confirmed ACN1762 possesses a single copy of the fusion construct. FIG. 18 shows the nucleic acid and amino acid sequences of a chimeric enzyme, the "tethered fusion" created by fusing the catechol 1,2-dioxygenase CatA (underlined), and part of the ACIAD1443 (orf1)-encoded protein from *Acinetobacter baylyi* ADP1 (double underlined) and the cytochrome P450 O-dealkylase GcoA from *Amycolatopsis* sp. ATCC 39116 (non-bold, no underlining).

The CatA-GcoA and CatA-Orf1-GcoA fusion/chimeric constructs may comprise all or substantially all of the amino acids of each of the indicated polypeptides. In certain instances, one or more of the polypeptides, open reading frames, synthetic sequences or other components of the fusion constructs may be truncated by the absence of one or more amino acids from either the C- or N-terminus of the native amino acid sequence. For example, a CatA-GcoA fusion may contain at least 90% or more of the amino acids that make up one or both of the CatA or GcoA polypeptides. In some embodiments, the fusion may contain at least 75%, 80%, 85%, 90%, 91%, 92%, 93%, 94%, 95%, 96%, 97%, 98% or 99% of the amino acids of a given component of the fusion.

The methods disclosed herein were also used to elucidate preferential point mutants of the *Amycolatopsis* sp. ATCC 39116 GcoA and GcoB proteins. FIG. 19 shows the nucleic acid and amino acid sequences of a variant cytochrome P450 O-dealkylase GcoA, which arose after evolution in *Acinetobacter baylyi* and was found to have one amino acid replacement relative to the parent protein from *Amycolatopsis* sp. ATCC 39116. The nucleotide change is: G to A at position 215 in the coding sequence (underlined). The amino acid change is G to D at position 72 in the amino acid sequence (underlined).

FIG. 20 shows the nucleic acid and amino acid sequences of a variant GcoB, which arose after evolution in *Acinetobacter baylyi* and was found to have one amino acid replacement relative to the parent protein from *Amycolatopsis* sp. ATCC 39116. The nucleotide change is: G to A at position 10 in the coding sequence (underlined). The amino acid change is A to T at position 4 in the amino acid sequence (underlined).

Expression of this fusion protein in one or more copies in an organism may confer the ability for the organism to metabolize or grow on guaiacol, guaethol, anisole, or catechol. However, a reductase as described herein may also be expressed in certain embodiments to facilitate O-demethylation reactions and growth of organisms on products derived from lignin.

Figure 5:
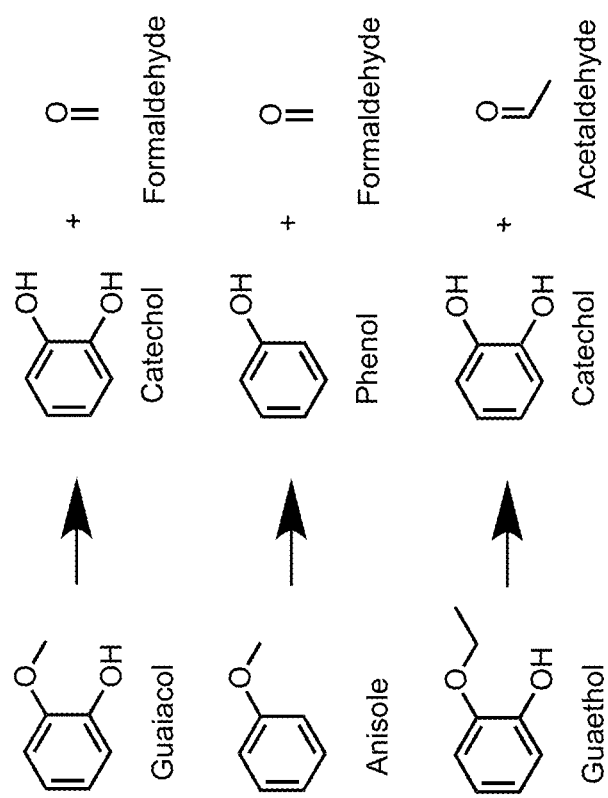
FIG. 5 shows exemplary dealkylation reactions catalyzed by the two component cytochrome P450 system.

Cytochrome P450 O-dealkylases or chimeric enzymes containing a catechol 1,2-dioxygenase and cytochrome P450 O-dealkylase activities may function in coordination with reductases to catalyze reactions such as the O-demethylation of guaiacol to catechol, the 0-demethylation of anisole to phenol, and the O-deethylation of guaethol to catechol (see FIG. 5). Generally, dealkylation is the removal of an alkyl group from a substrate, such as the removal of a methyl group to convert guaiacol to catechol and formaldehyde. These enzymes have activity not only on guaiacol, but also on anisole and guaethol. O-dealkylases may remove methyl, ethyl, propyl, butyl and other alkyl groups of the general formula $C_nH_{2n+1}$ from substrates. Another O-dealkylase activity may be to perform ether bond cleavage on aromatic compounds. In various embodiments, the enzymes may be from the CYP255 family of cytochrome P450 enzymes.

Some bacterial cytochrome P450 enzymes cooperate with one or two partner proteins, usually a reductase and a ferredoxin, that transfer electrons from a cofactor such as NAD(P)H to the cytochrome, though there are variations on this throughout prokaryotes and eukaryotes. In certain embodiments, the reductase may comprise a 2Fe-2S ferredoxin domain, a flavin adenine dinucleotide (FAD) binding region, a nicotinamide adenine dinucleotide (NAD) binding region or combinations thereof. For example, the reductase represented by SEQ ID NO:8 comprises an N-terminal 2Fe-2S ferredoxin domain followed by a FAD and NAD binding region with homology to ferredoxin-NADPH reductase (FNR) type oxidoreductases. This domain architecture is novel for a cytochrome P450 reductase, and the presence of both ferredoxin and NAD binding domains may indicate the reductase and the cytochrome P450, whose genes are natively clustered and transcribed together, form a two-component cytochrome P450 system.

The combination of both the cytochrome P450 and reductase polypeptides may be used as a two-component P450 system for dealkylating aromatic substrates, including demethylating guaiacol to produce catechol. For example, nucleic acid molecules encoding SEQ ID NOs: 4 and 8 encode a two-component cytochrome P450 system with guaiacol O-demethylase activity, as well as activity on other substrates including anisole (methoxybenzene), guaethol (2-ethoxyphenol), 2-propoxyphenol, and other substituted O-alkoxyphenols. Likewise, the chimeric enzymes described herein may be co-expressed with reductases to convert guaiacol to products such as catechol or cis,cis-muconic, or to allow organisms expressing both polypeptides to metabolize guaiacol. Additional enzymes for aromatic substrate conversion include enzymes from *Rhodococcus pyridinivorans* strains SB3094 (e.g., YP_008987954.1) and AK37 (e.g., WP_006553158.1), *Rhodococcus jostii* RHA1 (e.g., YP_702345.1) and *Amycolatopsis* sp. ATCC 39116 (previously known as *Streptomyces setonii* or *Streptomyces griseus* strain 75iv2). In some embodiments, the cytochrome P450 or reductase polypeptide may be from a species of the genera *Rhodococcus* (e.g., *R. pyridinivorans* or *R. jostii*) or *Amycolatopsis* (e.g., *Amycolatopsis* sp. ATCC 39116).

In various embodiments, the cytochrome P450, catechol 1,2-dioxygenase, or reductase polypeptides may be from microorganisms such as bacteria, yeast or fungi. Exemplary bacteria include species from the family Pseudonocardiaceae or species from the genera *Rhodococcus, Amycolatopsis, Acinetobacter, Pimelobacter, Gordonia, Pseudonocardia, Saccharomonospora, Corynebacterium, Actinopolyspora, Nocardia, Saccharopolyspora, Nocardioides,* or *Granulicoccus*. Though specific examples are provided herein, other examples of microbial cytochrome P450, catechol 1,2-dioxygenase and reductase polypeptides are within the scope of this disclosure.

Cytochrome P450 polypeptides may be combined with reductase polypeptides to form a functional two-component complex capable of dealkylating an aromatic substrate. One of both of the polypeptides may be used in purified form. One of both of the polypeptides may be expressed by a microbial biocatalyst to carry out dealkylation. A biocatalyst host cell may express one or more of the polypeptides, or one or more of the polypeptides may be added exogenously to a biocatalyst culture. The cytochrome P450 and reductase polypeptides may be from the same organism or from different organisms, and various combinations may be created and tested for enzymatic activity.

Also presented are microorganisms engineered to express the enzymes disclosed herein and their use to biologically dealkylate aromatic substrates. Dealkylation may be carried out be culturing such microorganisms with a material containing aromatic substrates (e.g., guaiacol, guaethol or anisole) and allowing the microorganisms to enzymatically complete the conversion. Any microorganism capable of carrying out the dealkylation of the substrate through the addition of enzymes disclosed herein may be suitable. Exemplary microorganisms include bacteria, such as those from the genus *Pseudomonas*. Specific examples include strains of *Pseudomonas putida*, such as *P. putida* KT2440.

Aromatic substrate-containing materials may be contacted with enzymes disclosed herein to dealkylate the substrate. As used herein, "aromatic substrate-containing materials" means any natural or processed materials comprising detectable amounts of aromatic substrate compounds such as guaiacol, catechol, guaethol or anisole. These may be derived from many sources, including lignocellulose, lignin, or oils derived from the pyrolysis of biomass of other lignocellulose or cellulose sources.

Suitable enzymes may be derived from microorganisms such as bacteria, fungi, yeast or the like via cell lysis and isolation techniques, or produced recombinantly. In some embodiments, a microorganism expressing the enzyme may be used directly as a biocatalyst to covert the aromatic substrate.

Enzymes described herein may be used as purified recombinant enzyme or as culture broths from cells that naturally produce the enzyme or that have been engineered to produce the enzyme. Enzymes can be added exogenously, or may be expressed and secreted directly from a microbial biocatalyst, or used internally by the microbial biocatalyst. Suitable organisms for enzyme expression include aerobic microorganisms such as aerobic bacteria.

Bio-oils and other aromatic substrate-containing materials may be contacted with enzymes at a concentration and a temperature for a time sufficient to achieve the desired amount of dealkylation. Suitable times for dealkylation range from a few hours to several days, and may be selected to achieve a desired amount of conversion. Exemplary reaction times include 1, 2, 3, 4, 5, 6, 7, 8, 9, 10, 11, or 12 hours; and 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 days. In some embodiments, reaction times may be one or more weeks.

The resulting catechol, phenol, cis,cis-muconic acid and the like may be further converted to products such as higher alcohols, hydrocarbons, or other advanced fuels via biological or chemical pathways, or combination thereof. Catechol, phenol cis,cis-muconic acid and other products may be recovered or isolated from cells, cell cultures or reactions by standard separation techniques for further upgrading. Dealkylation products may also be further metabolized by biocatalyst cells in the culture to additional products metabolically derived from a dealkylation product. These additional products may in turn be isolated from cells, cell cultures or reactions by standard separation techniques and may be further upgraded to additional fuels and chemicals.

Methods of fractionating, isolating or purifying dealkylation products (or further upgraded products) include a variety of biochemical engineering unit operations. For example, the reaction mixture or cell culture lysate may be filtered to separate solids from products present in a liquid portion. Dealkylation products may be further extracted from a solvent and/or purified using conventional methods. Exemplary methods for purification/isolation/separation of dealkylation products include at least one of affinity chromatography, ion exchange chromatography, solvent extraction, filtration, centrifugation, electrophoresis, hydrophobic interaction chromatography, gel filtration chromatography, reverse phase chromatography, chromatofocusing, differential solubilization, preparative disc-gel electrophoresis, isoelectric focusing, HPLC, and/or or reversed-phase HPLC.

Pyrolysis offers a straightforward approach for the deconstruction of plant cell wall polymers into pyrolysis oil or bio-oil, which may be fractionated and subsequently used in biological approaches to selectively upgrade some of the resulting fractions. Lignocellulose or lignin-containing materials may be subjected to pyrolysis processes to generate oils containing aromatic substrates. Exemplary lignocellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

SEQ ID NOS:1, 3, 5, 7, 9, 11 and 13 provide nucleic acid and amino acid sequences for exemplary enzymes for use in the disclosed methods. "Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning or assembling into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning or assembling) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having enzyme activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional cytochrome P450 O-dealkylase, catechol 1,2-dioxygenase or reductase or fusions thereof. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to a sequence represented herein. In other embodiments, the nucleic acids may be at least about 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein, or 80%, 81%, 82%, 83%, 84%, 85%, 86%, 87%, 88%, 89%, 90%, 91%, 92%, 93%, 94%, 95%, 96%, 97%, 98% or 99% identical to a sequence represented herein. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode the polypeptides that possess the enzymatic activities described herein or functional equivalents thereof. A functional equivalent includes fragments or variants of these that exhibit one or more of the enzymatic activities. As a result of the degeneracy of the genetic code, many nucleic acid sequences can encode a given polypeptide with a particular enzymatic activity. Such functionally equivalent variants are contemplated herein.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, assembling, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as *E. coli*; bacteria from the genera *Pseudomonas* (e.g., *P. putida* or *P. fluorescens*), *Acinetobacter* (e.g., strains of *A. baylyi* such as ADP1), *Bacillus* (e.g., *B. subtilis*, *B. megaterium* or *B. brevis*), *Caulobacter* (e.g., *C. crescentus*), Lactoccocus (e.g., *L. lactis*), *Streptomyces* (e.g., *S. coelicolor*), *Streptococcus* (e.g., *S. lividans*), and Corynybacterium (e.g., *C. glutamicum*); fungi from the genera *Trichoderma* (e.g., *T. reesei*, *T. viride*, *T. koningii*, or *T. harzianum*), *Penicillium* (e.g., *P. funiculosum*), *Humicola* (e.g., *H. insolens*), *Chrysosporium* (e.g., *C. lucknowense*), *Gliocladium*, *Aspergillus* (e.g., *A. niger*, *A. nidulans*, *A. awamori*, or *A. aculeatus*), *Fusarium*, *Neurospora*, *Hypocrea* (e.g., *H. jecorina*), and *Emericella*; yeasts from the genera *Saccharomyces* (e.g., *S. cerevisiae*), *Pichia* (e.g., *P. pastoris*), or *Kluyveromyces* (e.g., *K. lactis*). Cells from plants such as *Arabidopsis*, barley, citrus, cotton, maize, poplar, rice, soybean, sugarcane, wheat, switch grass, alfalfa, *miscanthus*, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from bacteria or fungi by direct transformation, in which DNA is mixed with the cells and taken up without any additional manipulation, by conjugation, electroporation, or other means known in the art. Expression vectors may be expressed by bacteria or fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing bacteria or fungi, for example, are available from ATCC. Media may be supplemented with aromatic substrates like guaiacol, guaethol or anisole for dealkylation reactions.

The nucleic acid molecules described herein encode the enzymes with amino acid sequences such as those represented by SEQ ID NOS:2, 4, 6, 8, 10, 12 and 14. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented in SEQ ID NOS:2, 4, 6, 8, 10, 12 and 14 or may include up to a certain integer number of amino acid alterations. Such protein or polypeptide variants retain enzymatic activity, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences set forth in SEQ ID NOS:2, 4, 6, 8, 10, 12 and 14 and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

EXAMPLES

Example 1

Fusion Protein Creation and Growth of Strains on Guaiacol

Figure 17:
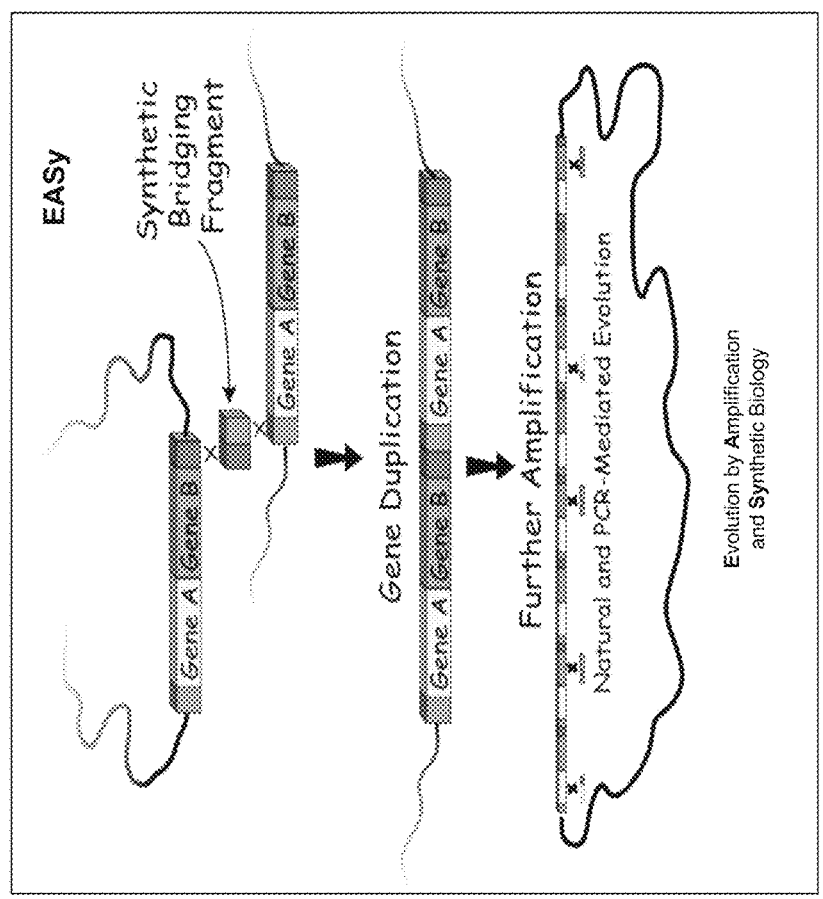
FIG. 17 shows an example of the Evolution by Amplification and Synthetic Biology methodology.

Two genes (gcoA and gcoB) were inserted into the *A. baylyi* ADP1 chromosome by allelic replacement. The genes gcoA and gcoB encode enzymes that convert guaiacol to catechol (FIG. 5). Although ADP1 naturally consumes catechol, it is unable to grow on guaiacol. The genes gcoA and gcoB in single copy on the chromosome did not permit growth on guaiacol. Attempts to select guaiacol-consuming strains were successful when these genes were amplified in a tandem chromosomal array. A linear synthetic bridging fragment was supplied to generate a precise chromosomal duplication of the region containing the foreign DNA (FIG. 17).

Most cells in a population select a common gene dosage that is beneficial for the specific amplicon and conditions. After inducing gene amplification, independent strains that grew on guaiacol as the sole carbon source were selected, and these strains required 8-10 copies of the gcoA/gcoB genes. Copy number was quantified with a real-time PCR (qPCR) assay. Continuous culturing was expected to allow the selection of isolates better able to degrade guaiacol. Improved growth might be reflected in faster growth, higher yields and/or growth on higher concentrations of guaiacol.

Figure 13:
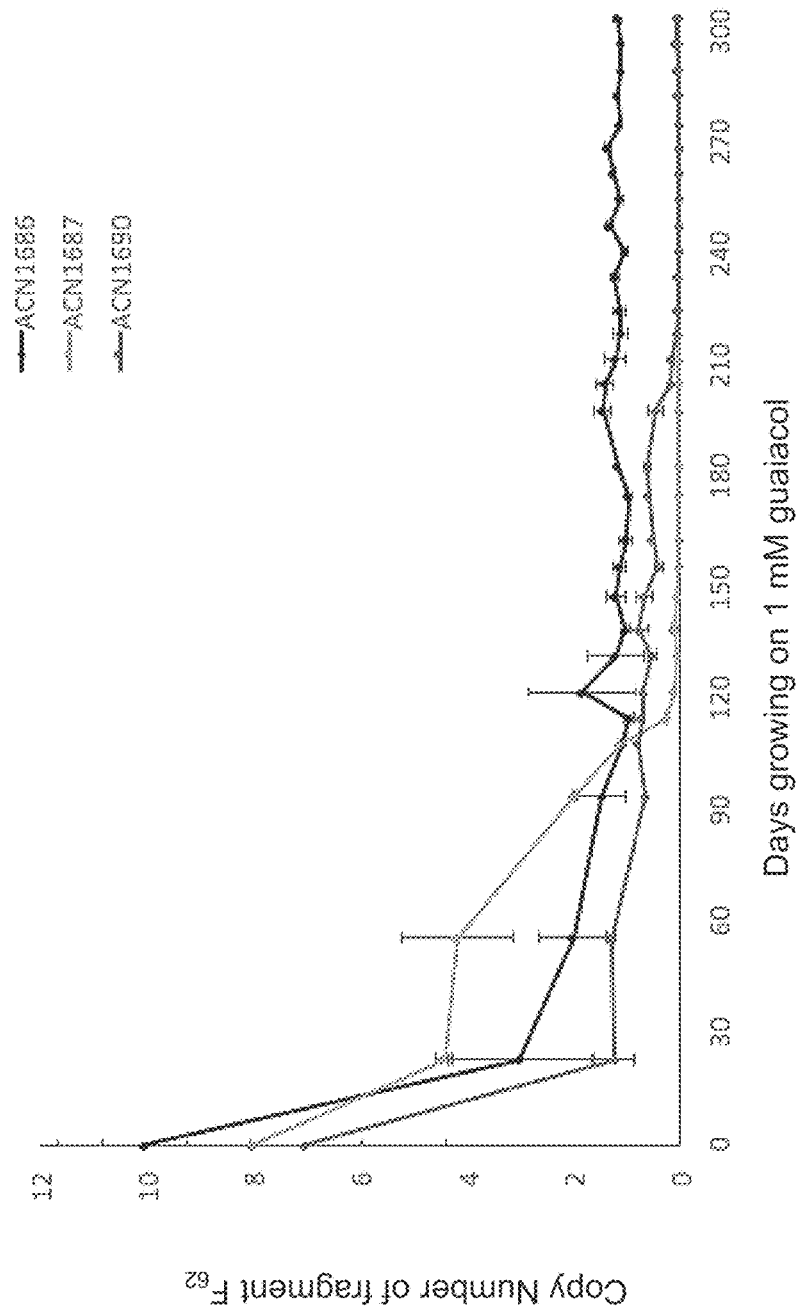
FIG. 13 shows gcoAB copy number during extended culture of *A. baylyi* containing fusion constructs.
Figure 14:
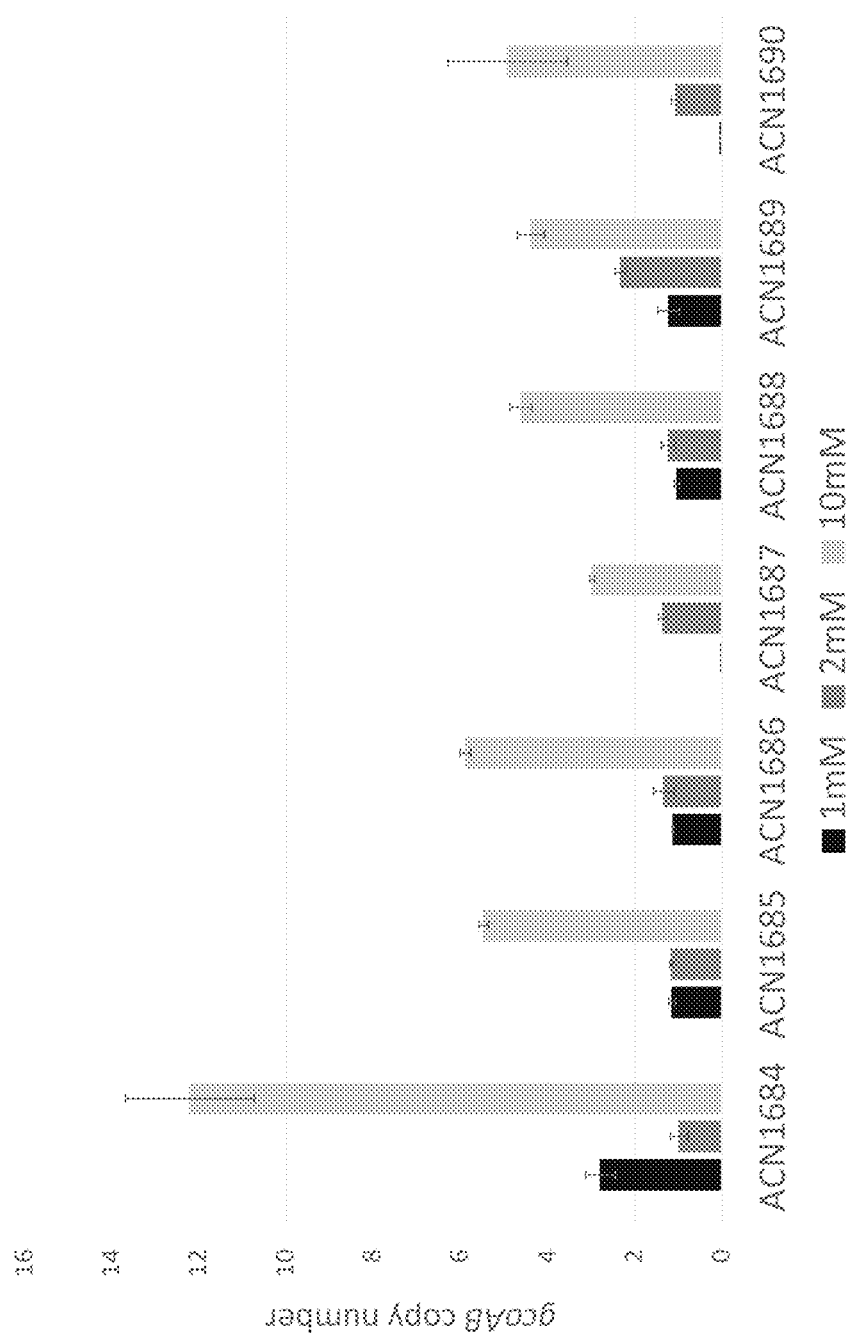
FIG. 14 shows gcoAB copy number during extended culture (290 days) of *A. baylyi* strains in the indicated concentration of guaiacol.
Figure 15:
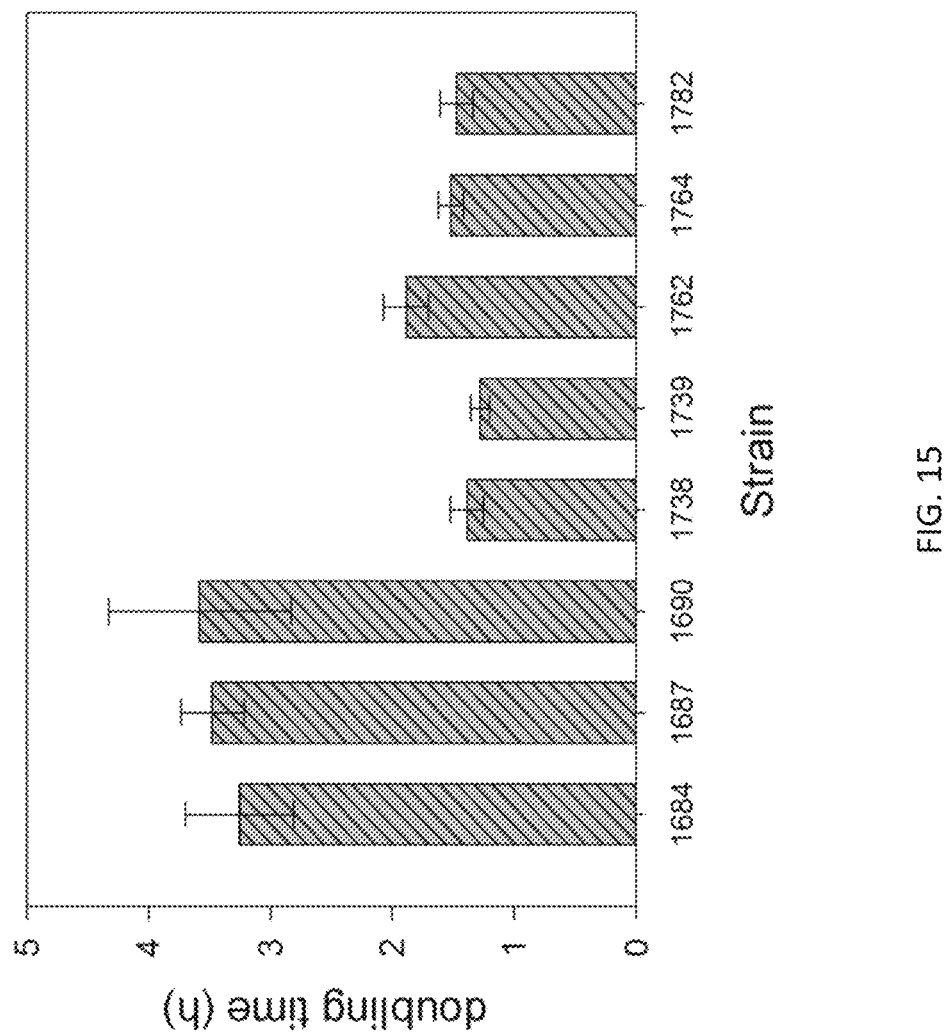
FIG. 15 shows the doubling times of various engineered *A. baylyi* strains growing on guaiacol as the sole carbon source.
Figure 16:
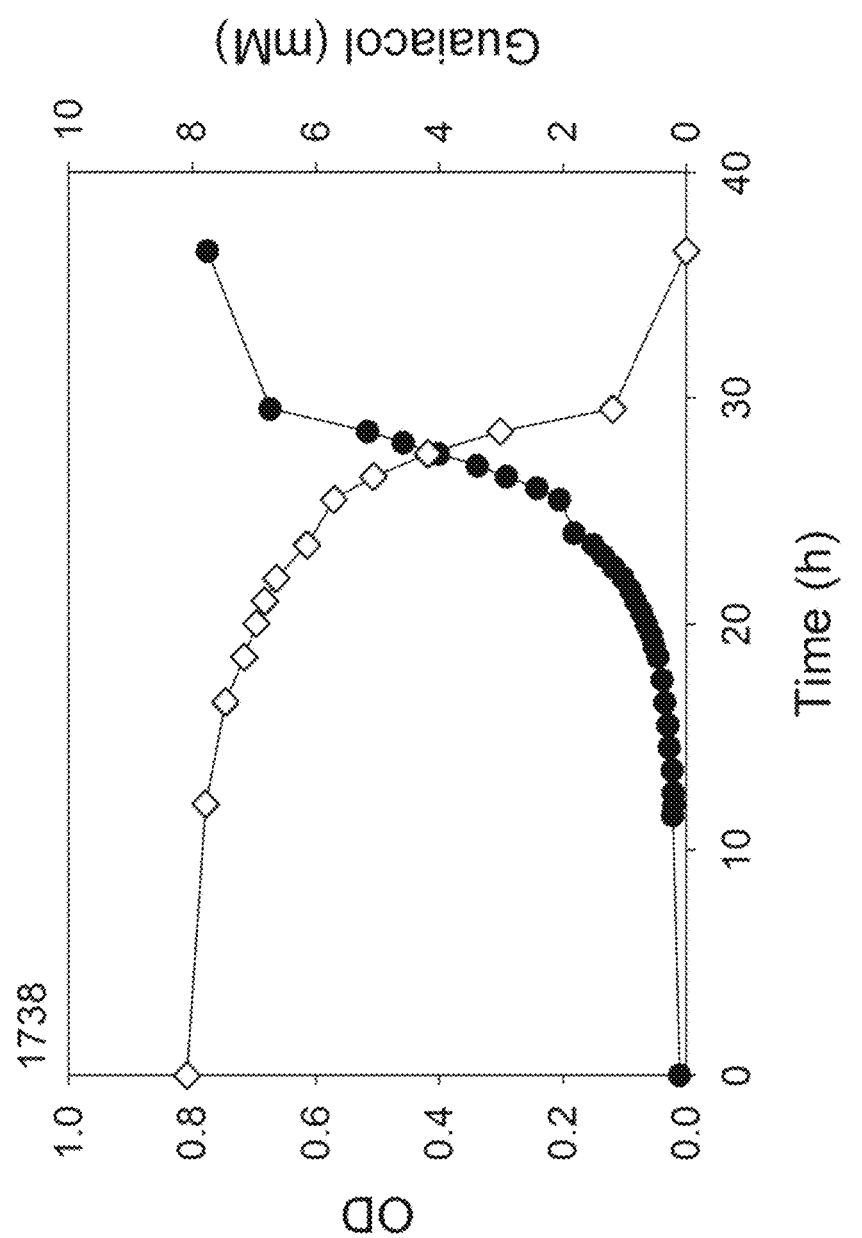
FIG. 16 shows guaiacol consumption by *A. baylyi* expressing the CatA-GcoA chimeric enzyme (ACN1738).

Over time, copy number was expected to decline because as gene performance improves through mutation, the pressure to maintain high copy number is reduced. Copy number was assessed by qPCR for mutant strains continuously selected using guaiacol as the sole carbon source. As predicted, copy number for the gco genes decreased in parallel lineages during extended culturing by serial transfer. FIG. 13 shows the results from two such cultures. Within several hundred generations, both populations yielded mutants with a single copy of the DNA on the chromosome. The results initially suggested that there were no copies of the gco genes (points indicating "0" on the Y axis). Sequence analysis revealed that there was in fact a single copy of the gcoAB genes in both mutants, but deletions removed sequence needed for the detection of the foreign gcoAB DNA in the qPCR assay. A single copy was therefore sufficient to allow growth on guaiacol.

In one instance, a spontaneous chromosomal deletion selected during growth on guaiacol was 295 bp long and removed DNA between gcoA and its upstream neighbor, catA, which encodes catechol 1,2-dioxygenase, the ring-cleavage dioxygenase for the conversion of catechol to cis,cis-muconic acid. This deletion also removed DNA encoding nine-amino acids in the C-terminus of CatA and three amino acids in the N-terminus of GcoA, thereby creating a chimeric protein.

Figure 6:
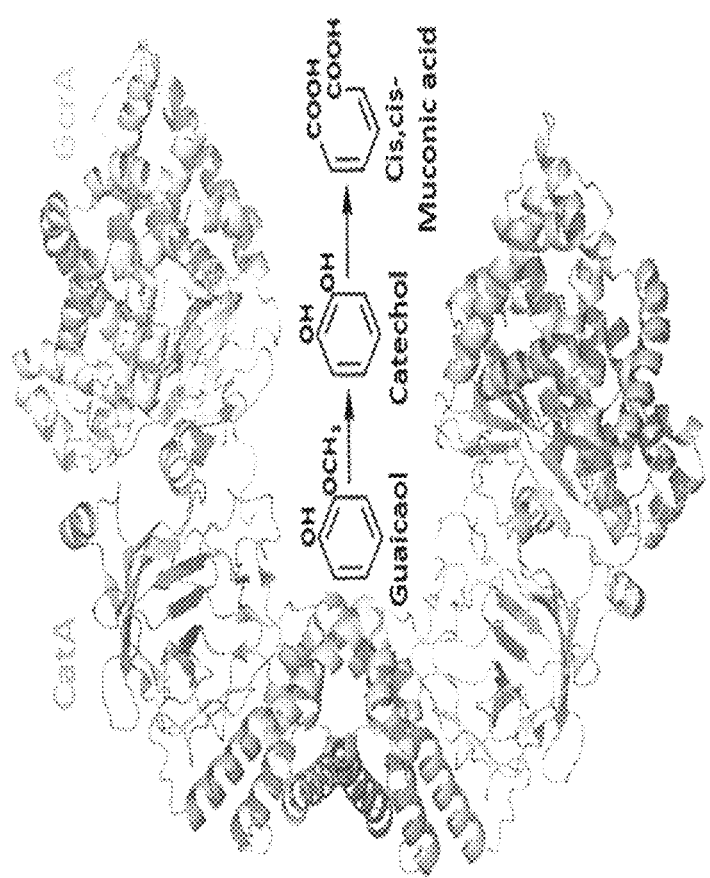
FIG. 6 shows a structural model of an exemplary CatA-GcoA chimeric enzyme and the conversion of guaiacol to catechol and subsequently to cis,cis-muconic acid.
Figure 7:
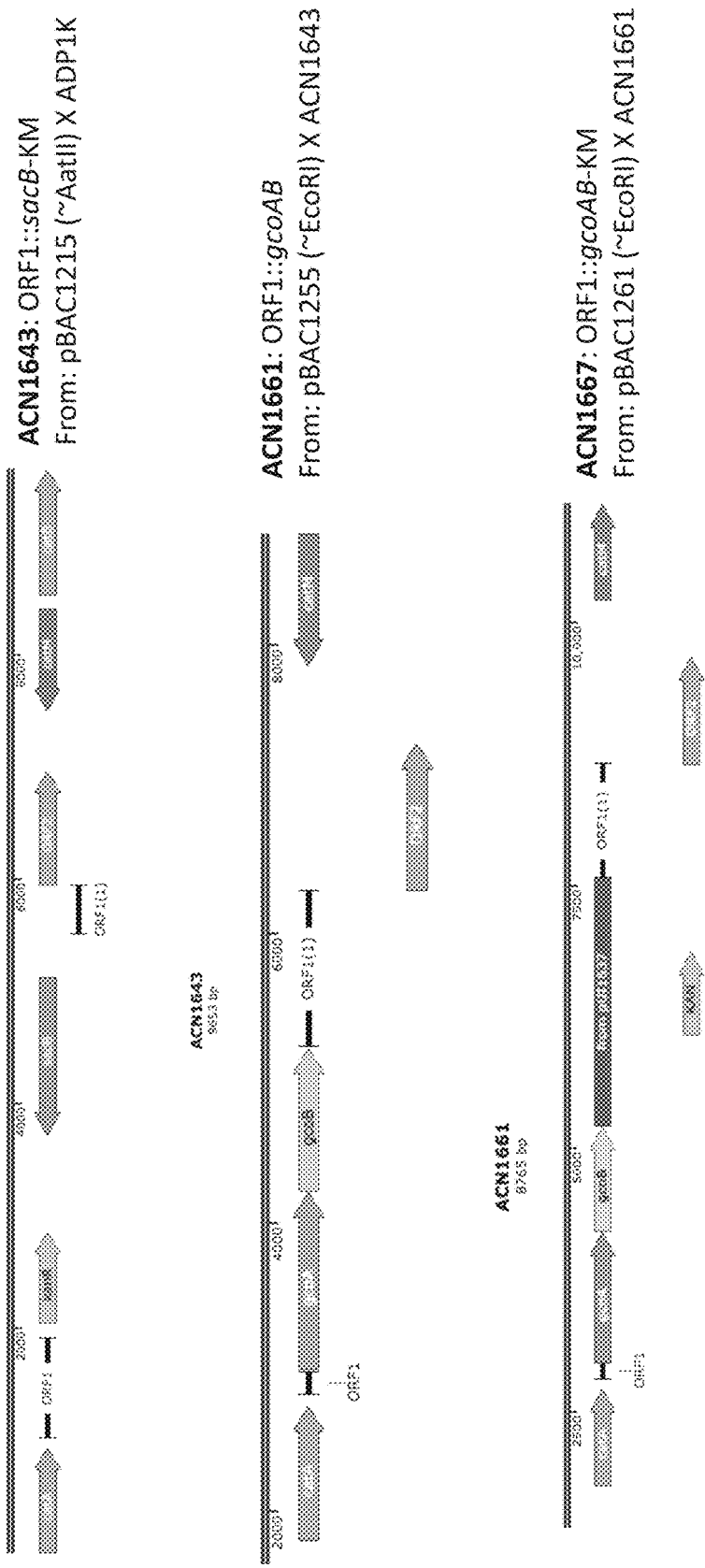
FIG. 7 shows schemes for the construction of parent strains for guaiacol degradation.
Figure 8:
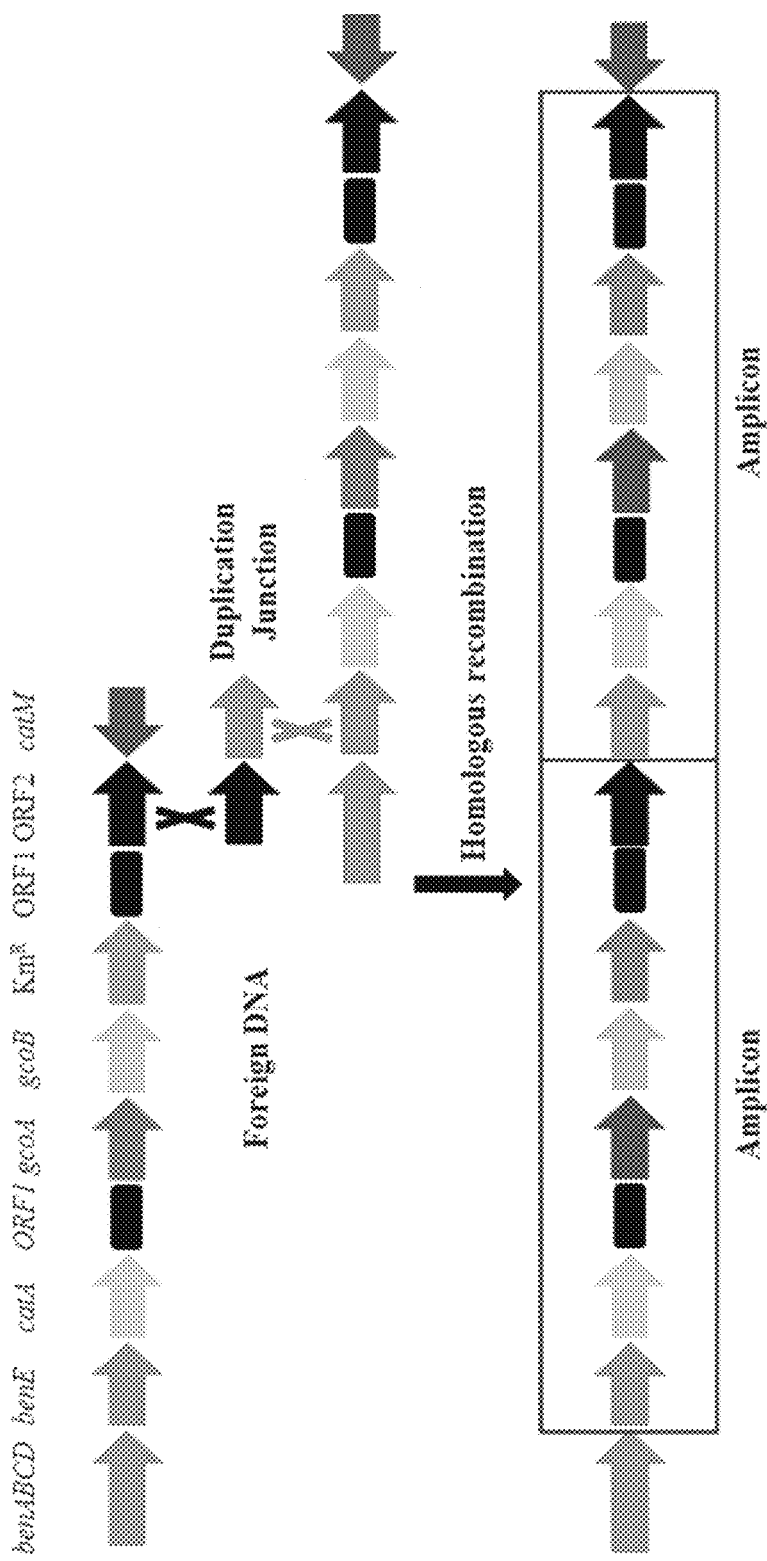
FIG. 8 shows a schematic for transformation with an engineered duplication junction.
Figure 9:
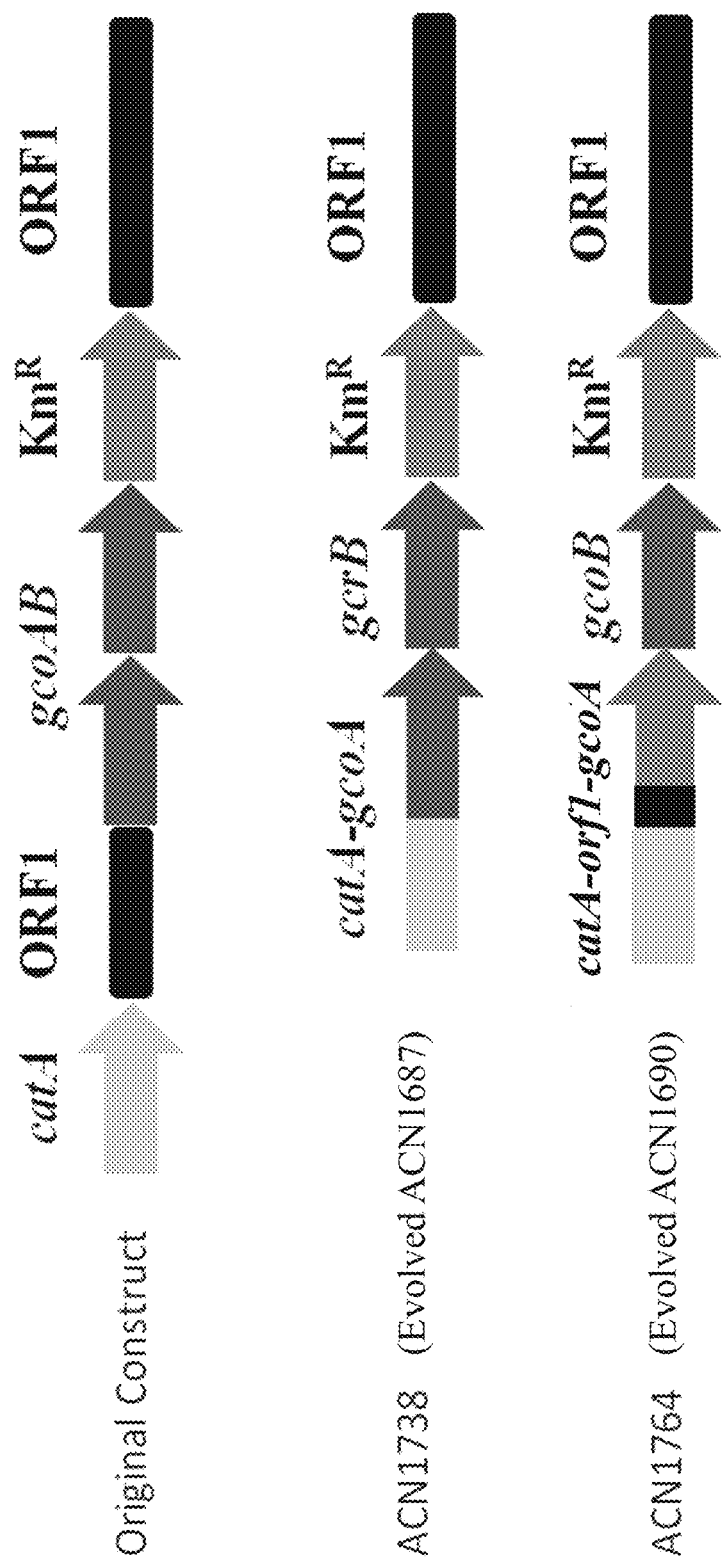
FIG. 9 shows diagrams of exemplary evolved fusion constructs.

FIG. 6 provides a structural model of the chimeric enzyme, with dimeric CatA (left) fused to GcoA (right side, upper and lower). By optimizing the diffusion distance between adjacent active sites, the chimera could prevent product inhibition of GcoA and efficiently channel catechol to CatA. Channeling could alleviate toxic effects of catechol by preventing its accumulation in vivo. The fused protein may help funnel catechol generated by GcoA directly to the CatA active site. The accumulation of catechol is known to be toxic in *Acinetobacter baylyi* ADP1. Insertion of a single copy of the gene fusion into a wild-type chromosome is all that is needed to confer the ability to grow on guaiacol. Not only is this allele sufficient in single copy, but the strain grows faster than the parent strain.

Example 2

Evolution by Amplification and Synthetic Biology (EASy) Methodology

A method of experimental evolution (termed EASy) that allows the rapid optimization of genetic regions and harnesses the extremely high efficiency of natural transformation and allelic exchange in *A. baylyi* was developed. The basis of this method is to create amplified regions of DNA on the chromosome which provide some selectable function. After amplification, the cells are grown under conditions that allow copy number to change and accelerate the emergence of new mutants.

The concept of gene duplication and divergence is central to evolutionary theory. Many evolutionary models now describe a period of transient gene amplification. According to these models, gene duplication, which increases the amount of a protein with a weak side activity, is selected when that activity is beneficial. Selective pressure can maintain additional gene copies (further amplification) that result occasionally from homologous recombination. In *A. baylyi*, gene amplification and selection result in the retention of large amounts of amplified DNA (often more than ~1 Mb) in addition to the normal ~4 Mb genome. Multiple gene copies provide a large DNA target for point mutations, indels, and rearrangements. If such mutations increase fitness, selection for multiple gene copies will decrease, and the repetitive DNA tends to be deleted. Gene amplification, as documented in experimental evolution studies, occurs sporadically and may take thousands of generations to enable a new trait to emerge.

In the method, called EASy (FIG. 17), DNA fragments are designed to accelerate and direct the process. Transformation of *A. baylyi* with a 'synthetic bridging fragment' induces a precise chromosomal duplication by serving as a template for homologous recombination ("x" in FIG. 17). Under selection, the duplicated DNA adjusts to gene dosage determined by the conditions. An amplified chromosomal array of genetic modules has been established. During extended culturing, new alleles were selected and copy number decreased. One unique aspect of this method is the ability to induce amplification so that experiments start with an amplified DNA array. By eliminating the initial phase of rare, stochastic amplification, novel traits can emerge rapidly. In Example 1 above, this method enabled ADP1 to grow on guaiacol, a lignin-derived aromatic compound that it does not naturally degrade. New alleles emerged within several hundred generations. Table 1 shows strains of *A. baylyi* and plasmids generated using the methods described herein, along with relevant characteristics of each. Included in the table are strains encoding the GcoAB variant, discovered via EASy evolution of ACN1686.

TABLE 1

Strains and Plasmids

Relevant Characteristics

| *A. baylyi* Strain | |
|---|---|
| ADP1 | Wild-type (BD413) |
| ACN1667 | orf1::gcoAB-Km$^R$ 51667; Guaiacol− parent |
| ACN1676 | ACN1667-derived, orf2benE51676 engineered junction; (1 mg/mL Km$^R$), Guaiacol− parent |
| ACN1684-1690 | ACN1676-derived, orf2benE51676 engineered junction; Guaiacol+ |
| ACN1738 | Evolved ACN1687, orf2benE51676 engineered junction; catA- gcoA51687; Guaiacol+ |
| ACN1764 | Evolved ACN1690, orf2benE51676 engineered junction; catA-orf1-gcoA51690; Guaiacol+ |
| ACN1739 | ACN1687 reconstructed strain derived by transforming with catA-gcoA51687 (from gap-repaired plasmid); Guaiacol+ |
| ACN1762 | ACN1690 reconstructed strain derived by transforming with catA-orf1-gcoA51690 (from gap-repaired plasmid); Guaiacol+ |
| ACN1686 | ACN1676-derived, orf2benE51676 engineered junction; Guaiacol+ (amplification, mixed population) |
| ACN1850 | Derived from ACN1686 by EASy method. Single copy of gcoAB-Km$^R$ region. Guaiacol+ gcoA51850 (encodes GcoA[G72D]) and gcoB51850 encodes (GcoB[A4T]) |
| ACN1863 | Reconstructed strain engineered to carry gcoB51850 encodes (GcoB[A4T]) in the ACN1667 background of an otherwise wild-type strain. Guaiacol− |
| ACN1881 | Reconstructed strain engineered to carry gcoA51850 encodes (GcoA[G72F]) in the ACN1667 background of an otherwise wild-type strain. Guaiacol− by colony assessment; However, appears to enable slow growth on guaiacol that permits spontaneous Guaiacol+ colonies to form on plates |
| ACN1886 | Reconstructed strain engineered to carry gcoA51850, which encodes (GcoA[G72F]), and gcoB51850, which encodes (GcoB[A4T]), in the ACN1667 background of an otherwise wild-type strain. Guaiacol− by colony assessment; However, appears to enable slow growth on guaiacol that permits spontaneous Guaiacol+ colonies to form on plates |
| Plasmid | |
| pBAC1314 | ApR, KmR; catA-gcoA51687; fragment recovered from ACN1687 in pBAC1282 |
| pBAC1337 | ApR, KmR; catA-orf1-gcoA51690; fragment recovered from ACN1690 in pBAC1282 |

Figure 21:
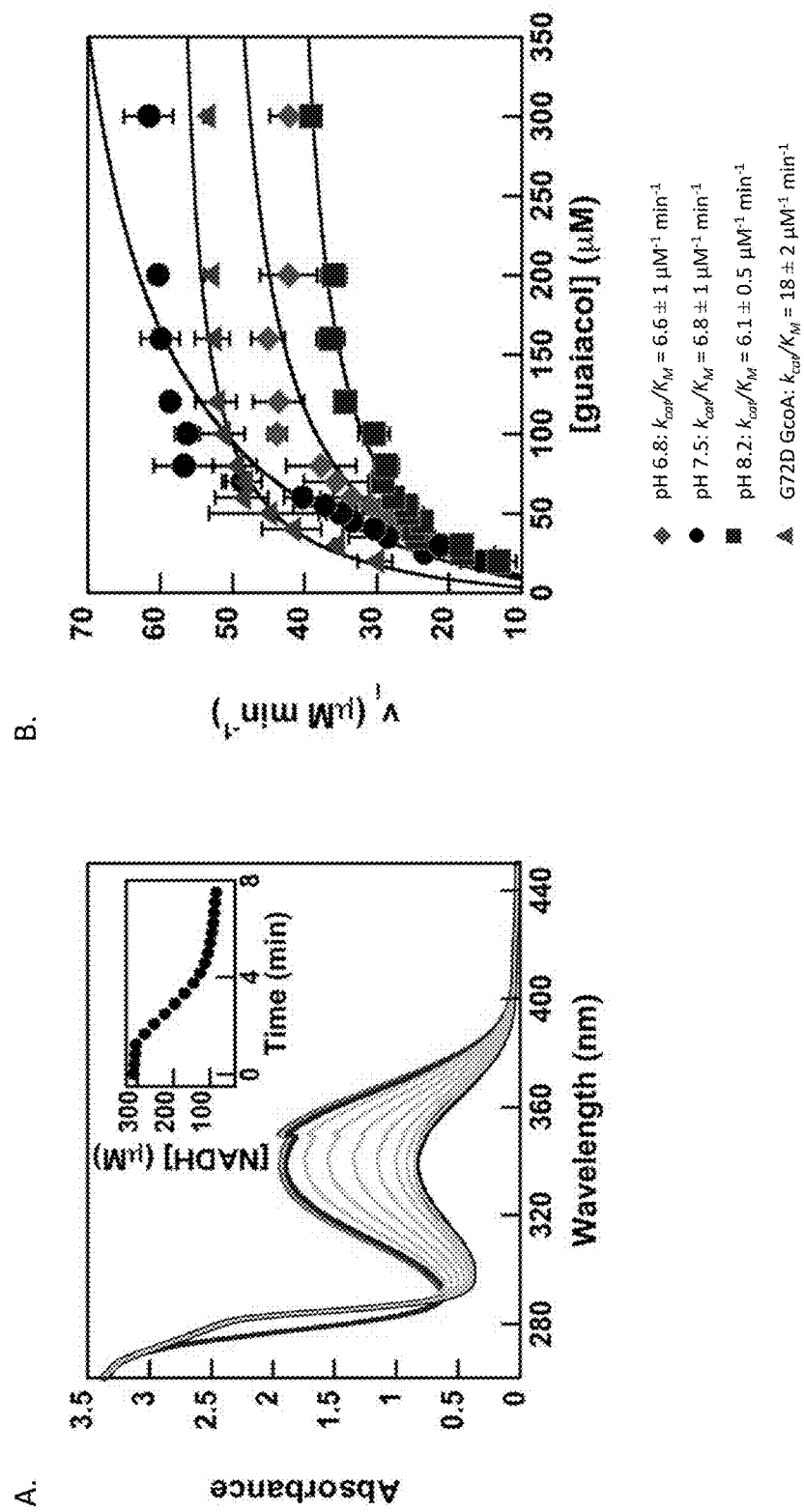
FIG. 21 shows NADH consumption monitored during guaiacol demethylation to yield kinetic values: NADH oxidation is monitored over time at 340 nm (A) and fit to the Michaelis-Menten model to get values of $k_{cat}/K_M$ (B).

UV/Vis spectroscopy can be used to follow the progress of the GcoAB enzymatic reaction and to obtain kinetic parameters for enzymes. NADH consumption can be monitored during guaiacol demethylation to yield kinetic values (GcoAB converts NADH and guaiacol to NAD$^+$, catechol and formaldehyde). Panel A of FIG. 21 shows NADH oxidation monitored over time at 340 nm while Panel B shows the resulting data fit to the Michaelis-Menten model to get values of $k_{cat}/K_M$ for the indicated enzymes under the indicated conditions. The results demonstrate that the GcoA [G72D] variant exhibits an increased catalytic efficiency compared to the native GcoA.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. An isolated DNA molecule encoding a chimeric enzyme comprising a cytochrome P450 polypeptide and a catechol 1,2-dioxygenase polypeptide, wherein the chimeric enzyme comprises at least 90% of the amino acids of SEQ ID NO: 4.

2. The isolated DNA molecule of claim 1, wherein the chimeric enzyme further comprises at least 90% of the amino acids of SEQ ID NO: 6.

3. The isolated DNA molecule of claim 2, wherein the chimeric enzyme has an amino acid sequence at least 90% identical to SEQ ID NO:2 or SEQ ID NO:10.

4. The isolated DNA molecule of claim 3, wherein the chimeric enzyme has the amino acid sequence of SEQ ID No:2 or SEQ ID NO: 10.

5. The isolated DNA molecule of claim 1, further comprising an exogenous promoter operably linked to the DNA molecule.

6. An expression vector comprising the DNA molecule of claim 1.

7. A host cell that expresses a recombinant polypeptide encoded by the DNA molecule of claim 1.

8. The host cell of claim 7, wherein the cell is from a strain of Pseudomonas or Acinetobacter.

9. The host cell of claim 8, wherein the cell is P. putida.

10. A method for removing an alkyl group from an aromatic substrate, comprising contacting a material containing the aromatic substrate with the chimeric enzyme encoded by the isolated DNA molecule of claim 1.

11. The method of claim 10, wherein the contacting step comprises culturing a microorganism with the material containing the aromatic substrate, wherein the microorganism expresses the chimeric enzyme.

12. The method of claim 10, wherein the aromatic substrate comprises guaiacol, catechol, anisole or guaethol.

13. The method of claim 10, wherein the material containing the aromatic substrate comprises products of lignin depolymerization.

14. The method of claim 10, wherein the material containing the aromatic substrate comprises a pyrolysis oil or bio-oil.

15. The method of claim 10, wherein the chimeric enzyme is encoded by the isolated DNA molecule of claim 2.

16. The method of claim 10, wherein the chimeric enzyme has an amino acid sequence at least 90% identical to SEQ ID NO: 2 or SEQ ID NO: 10.

17. The method of claim 10, wherein the dealkylation product is catechol, phenol or cis,cis-muconic acid.

18. The method of claim 10, further comprising isolating the dealkylation product.

* * * * *

SEQUENCE LISTING

```
<160> NUMBER OF SEQ ID NOS: 14

<210> SEQ ID NO 1
<211> LENGTH: 2118
<212> TYPE: DNA
<213> ORGANISM: Artificial Sequence
<220> FEATURE:
<223> OTHER INFORMATION: Chimeric construct
<220> FEATURE:
<221> NAME/KEY: CDS
<222> LOCATION: (1)..(2118)

<400> SEQUENCE: 1 atg gaa gtt aaa ata ttc aat act cag gat gtg caa gat ttt tta cgt      48
Met Glu Val Lys Ile Phe Asn Thr Gln Asp Val Gln Asp Phe Leu Arg
1               5                   10                  15 gtt gca agc gga ctt gag caa gaa ggt ggc aat ccg cgt gta aag cag      96
Val Ala Ser Gly Leu Glu Gln Glu Gly Gly Asn Pro Arg Val Lys Gln
            20                  25                  30 atc atc cat cgt gtg ctt tca gat tta tat aaa gcc att gaa gat ttg     144
Ile Ile His Arg Val Leu Ser Asp Leu Tyr Lys Ala Ile Glu Asp Leu
        35                  40                  45 aat atc act tca gat gaa tac tgg gca ggt gtg gca tat tta aat cag     192
Asn Ile Thr Ser Asp Glu Tyr Trp Ala Gly Val Ala Tyr Leu Asn Gln
    50                  55                  60 cta ggt gcc aat caa gaa gct ggt tta ctc tcg cca ggc ttg ggt ttt     240
Leu Gly Ala Asn Gln Glu Ala Gly Leu Leu Ser Pro Gly Leu Gly Phe
65                  70                  75                  80 gac cat tac ctc gat atg cgt atg gat gcc gaa gat gcc gca cta ggt     288
Asp His Tyr Leu Asp Met Arg Met Asp Ala Glu Asp Ala Ala Leu Gly
                85                  90                  95 att gaa aat gcg aca cca cgt acc att gaa ggc ccg cta tac gtg gca     336
Ile Glu Asn Ala Thr Pro Arg Thr Ile Glu Gly Pro Leu Tyr Val Ala
            100                 105                 110 ggt gcg cct gaa tcg gta ggt tat gcg cgc atg gat gac gga agt gat     384
Gly Ala Pro Glu Ser Val Gly Tyr Ala Arg Met Asp Asp Gly Ser Asp
        115                 120                 125 cca aat ggt cat acc ctg att cta cat ggc acg atc ttt gat gca gat     432
Pro Asn Gly His Thr Leu Ile Leu His Gly Thr Ile Phe Asp Ala Asp
    130                 135                 140 gga aaa cct tta ccc aat gcc aaa gtt gaa atc tgg cat gcc aat acc     480
Gly Lys Pro Leu Pro Asn Ala Lys Val Glu Ile Trp His Ala Asn Thr
145                 150                 155                 160 aaa ggc ttt tat tca cac ttc gac cca aca ggc gag cag cag gcg ttc     528
Lys Gly Phe Tyr Ser His Phe Asp Pro Thr Gly Glu Gln Gln Ala Phe
                165                 170                 175 aat atg cgc cgt agt att att acc gat gaa aac ggt cag tat cgc gtt     576
Asn Met Arg Arg Ser Ile Ile Thr Asp Glu Asn Gly Gln Tyr Arg Val
            180                 185                 190 cgt acc att ttg cct gcg ggt tat ggt tgc cca cca gaa ggt cca acg     624
Arg Thr Ile Leu Pro Ala Gly Tyr Gly Cys Pro Pro Glu Gly Pro Thr
        195                 200                 205
```

-continued

| | | |
|---|---|---|
| caa cag ttg ctg aat cag ttg ggc cgt cat ggt aac cgc cct gcg cac<br>Gln Gln Leu Leu Asn Gln Leu Gly Arg His Gly Asn Arg Pro Ala His<br>210                         215                          220 | | 672 |
| att cac tat ttt gtt tct gcc gat gga cac cgc aaa cta act acg caa<br>Ile His Tyr Phe Val Ser Ala Asp Gly His Arg Lys Leu Thr Thr Gln<br>225                         230                       235                240 | | 720 |
| att aat gtg gct ggc gat ccg tac acc tat gac gac ttt gct tat gca<br>Ile Asn Val Ala Gly Asp Pro Tyr Thr Tyr Asp Asp Phe Ala Tyr Ala<br>                         245                       250                     255 | | 768 |
| acc cgt gaa ggc ttg gtg gtt gat gca gtg gaa cac acc gat cct gaa<br>Thr Arg Glu Gly Leu Val Val Asp Ala Val Glu His Thr Asp Pro Glu<br>          260                     265                     270 | | 816 |
| gcc att aag gcc aat gat gtt gaa ggc cca ttc gct gaa atg gtt ttc<br>Ala Ile Lys Ala Asn Asp Val Glu Gly Pro Phe Ala Glu Met Val Phe<br>275                       280                       285 | | 864 |
| gat cta aaa ttg acg cgt ttg gtt gat ggt gta gat aac caa acc gaa<br>Asp Leu Lys Leu Thr Arg Leu Val Asp Gly Val Asp Asn Gln Thr Glu<br>290                       295                    300 | | 912 |
| cgg ccc gat ctc gcc tgg ctc gac gag gtc acc atg acg cag ctc gag<br>Arg Pro Asp Leu Ala Trp Leu Asp Glu Val Thr Met Thr Gln Leu Glu<br>305                       310                    315              320 | | 960 |
| cgc aac ccg tac gag gtg tac gag cgg ctg cgc gcg gag gcg ccg ctg<br>Arg Asn Pro Tyr Glu Val Tyr Glu Arg Leu Arg Ala Glu Ala Pro Leu<br>                       325                     330                335 | | 1008 |
| gcc ttc gtg ccg gtg ctg ggg tcc tac gtc gcc tcg acc gcc gag gtc<br>Ala Phe Val Pro Val Leu Gly Ser Tyr Val Ala Ser Thr Ala Glu Val<br>          340                     345                     350 | | 1056 |
| tgc cgc gaa gtc gcg acc agc ccg gac ttc gag gcc gtc atc acc ccg<br>Cys Arg Glu Val Ala Thr Ser Pro Asp Phe Glu Ala Val Ile Thr Pro<br>               355                     360                   365 | | 1104 |
| gcc ggc ggc cgc acc ttc ggg cac ccg gcg atc atc ggc gtc aac ggc<br>Ala Gly Gly Arg Thr Phe Gly His Pro Ala Ile Ile Gly Val Asn Gly<br>370                       375                     380 | | 1152 |
| gac atc cac gcc gac ctg cgc tcc atg gtc gag ccc gcc ctg cag ccc<br>Asp Ile His Ala Asp Leu Arg Ser Met Val Glu Pro Ala Leu Gln Pro<br>385                       390                    395              400 | | 1200 |
| gcc gag gtg gac cgc tgg atc gac gac ctg gtg cgg ccc atc gcg cgc<br>Ala Glu Val Asp Arg Trp Ile Asp Asp Leu Val Arg Pro Ile Ala Arg<br>                       405                     410                415 | | 1248 |
| cgc tac ctg gag cgg ttc gaa aac gac ggg cac gcc gaa ctg gtg gcg<br>Arg Tyr Leu Glu Arg Phe Glu Asn Asp Gly His Ala Glu Leu Val Ala<br>          420                     425                     430 | | 1296 |
| cag tac tgc gag ccg gtc agc gtc cgc tcg ctc ggc gac ctg ctc ggc<br>Gln Tyr Cys Glu Pro Val Ser Val Arg Ser Leu Gly Asp Leu Leu Gly<br>               435                     440                   445 | | 1344 |
| ctg cag gag gtc gac tcg gac aag ctg cgc gag tgg ttc gcc aag ctg<br>Leu Gln Glu Val Asp Ser Asp Lys Leu Arg Glu Trp Phe Ala Lys Leu<br>450                       455                    460 | | 1392 |
| aac cgc tcg ttc acc aac gcc gcc gtc gac gag aac ggc gag ttc gcc<br>Asn Arg Ser Phe Thr Asn Ala Ala Val Asp Glu Asn Gly Glu Phe Ala<br>465                       470                    475              480 | | 1440 |
| aac ccc gag ggc ttc gcc gag ggc gac cag gcg aag gcc gag atc cgc<br>Asn Pro Glu Gly Phe Ala Glu Gly Asp Gln Ala Lys Ala Glu Ile Arg<br>                       485                     490                495 | | 1488 |
| gcc gtc gtc gac ccg ctg atc gac aag tgg atc gag cac ccc gac gac<br>Ala Val Val Asp Pro Leu Ile Asp Lys Trp Ile Glu His Pro Asp Asp<br>          500                     505                     510 | | 1536 |
| agc gcc att tcg cac tgg ctg cac gac ggc atg ccg ccc ggc cag acc<br>Ser Ala Ile Ser His Trp Leu His Asp Gly Met Pro Pro Gly Gln Thr<br>               515                     520                   525 | | 1584 |

| | | | | | | | | | | | | | | | |
|---|---|---|---|---|---|---|---|---|---|---|---|---|---|---|---|
| cgc | gac | cgc | gag | tac | atc | tac | ccg | acg | atc | tac | gtg | tac | ctg | ctc | ggc | 1632 |
| Arg | Asp | Arg | Glu | Tyr | Ile | Tyr | Pro | Thr | Ile | Tyr | Val | Tyr | Leu | Leu | Gly |
| | | 530 | | | | 535 | | | | 540 | | | | | |

```
cgc gac cgc gag tac atc tac ccg acg atc tac gtg tac ctg ctc ggc     1632
Arg Asp Arg Glu Tyr Ile Tyr Pro Thr Ile Tyr Val Tyr Leu Leu Gly
        530                 535                 540 gcg atg cag gaa ccc ggc cac ggc atg gcc tcc acc ctg gtc ggc ctg     1680
Ala Met Gln Glu Pro Gly His Gly Met Ala Ser Thr Leu Val Gly Leu
545                 550                 555                 560 ttc agc agg ccc gag cag ctg gaa gag gtg gtc gac gac ccc acg ctg     1728
Phe Ser Arg Pro Glu Gln Leu Glu Glu Val Val Asp Asp Pro Thr Leu
                565                 570                 575 atc ccg cgg gcg atc gcc gag ggc ctg cgg tgg acc tcg ccg atc tgg     1776
Ile Pro Arg Ala Ile Ala Glu Gly Leu Arg Trp Thr Ser Pro Ile Trp
                580                 585                 590 tcg gcc acc gcc cgc atc tcc acc aag ccg gtg acc atc gcc ggg gtc     1824
Ser Ala Thr Ala Arg Ile Ser Thr Lys Pro Val Thr Ile Ala Gly Val
            595                 600                 605 gac ctg ccc gcc ggc acg ccg gtg atg ctc tcc tac ggc tcg gcc aac     1872
Asp Leu Pro Ala Gly Thr Pro Val Met Leu Ser Tyr Gly Ser Ala Asn
610                 615                 620 cac gac acc ggc aag tac gag gcg ccc tcg cag tac gac ctg cac cgc     1920
His Asp Thr Gly Lys Tyr Glu Ala Pro Ser Gln Tyr Asp Leu His Arg
625                 630                 635                 640 ccg ccg ctg ccg cac ctc gcc ttc ggc gcg ggc aac cac gcg tgc gcg     1968
Pro Pro Leu Pro His Leu Ala Phe Gly Ala Gly Asn His Ala Cys Ala
                645                 650                 655 ggc atc tac ttc gcc aac cac gtc atg cgg atc gcg ctg gag gag ctg     2016
Gly Ile Tyr Phe Ala Asn His Val Met Arg Ile Ala Leu Glu Glu Leu
                660                 665                 670 ttc gag gcc atc ccg aac ctg gag cgc gac acc cgc gag ggc gtc gag     2064
Phe Glu Ala Ile Pro Asn Leu Glu Arg Asp Thr Arg Glu Gly Val Glu
            675                 680                 685 ttc tgg ggc tgg ggc ttc cgc ggc ccc acc tcg ctg cac gtc acc tgg     2112
Phe Trp Gly Trp Gly Phe Arg Gly Pro Thr Ser Leu His Val Thr Trp
        690                 695                 700 gag gtg                                                             2118
Glu Val
705

<210> SEQ ID NO 2
<211> LENGTH: 706
<212> TYPE: PRT
<213> ORGANISM: Artificial Sequence
<220> FEATURE:
<223> OTHER INFORMATION: Synthetic Construct

<400> SEQUENCE: 2

Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Pro Gly Leu Gly Phe
65                  70                  75                  80

Asp His Tyr Leu Asp Met Arg Met Asp Ala Glu Asp Ala Ala Leu Gly
                85                  90                  95

Ile Glu Asn Ala Thr Pro Arg Thr Ile Glu Gly Pro Leu Tyr Val Ala
            100                 105                 110
```

-continued

Gly Ala Pro Glu Ser Val Gly Tyr Ala Arg Met Asp Asp Gly Ser Asp
            115                 120                 125

Pro Asn Gly His Thr Leu Ile Leu His Gly Thr Ile Phe Asp Ala Asp
            130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
            195                 200                 205

Gln Gln Leu Leu Asn Gln Leu Gly Arg His Gly Asn Arg Pro Ala His
            210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Asp Phe Ala Tyr Ala
                245                 250                 255

Thr Arg Glu Gly Leu Val Val Asp Ala Val Glu His Thr Asp Pro Glu
            260                 265                 270

Ala Ile Lys Ala Asn Asp Val Glu Gly Pro Phe Ala Glu Met Val Phe
            275                 280                 285

Asp Leu Lys Leu Thr Arg Leu Val Asp Gly Val Asp Asn Gln Thr Glu
            290                 295                 300

Arg Pro Asp Leu Ala Trp Leu Asp Glu Val Thr Met Thr Gln Leu Glu
305                 310                 315                 320

Arg Asn Pro Tyr Glu Val Tyr Glu Arg Leu Arg Ala Glu Ala Pro Leu
                325                 330                 335

Ala Phe Val Pro Val Leu Gly Ser Tyr Val Ala Ser Thr Ala Glu Val
            340                 345                 350

Cys Arg Glu Val Ala Thr Ser Pro Asp Phe Glu Ala Val Ile Thr Pro
            355                 360                 365

Ala Gly Gly Arg Thr Phe Gly His Pro Ala Ile Ile Gly Val Asn Gly
            370                 375                 380

Asp Ile His Ala Asp Leu Arg Ser Met Val Glu Pro Ala Leu Gln Pro
385                 390                 395                 400

Ala Glu Val Asp Arg Trp Ile Asp Asp Leu Val Arg Pro Ile Ala Arg
                405                 410                 415

Arg Tyr Leu Glu Arg Phe Glu Asn Asp Gly His Ala Glu Leu Val Ala
            420                 425                 430

Gln Tyr Cys Glu Pro Val Ser Val Arg Ser Leu Gly Asp Leu Leu Gly
            435                 440                 445

Leu Gln Glu Val Asp Ser Asp Lys Leu Arg Glu Trp Phe Ala Lys Leu
450                 455                 460

Asn Arg Ser Phe Thr Asn Ala Ala Val Asp Glu Asn Gly Glu Phe Ala
465                 470                 475                 480

Asn Pro Glu Gly Phe Ala Glu Gly Asp Gln Ala Lys Ala Glu Ile Arg
                485                 490                 495

Ala Val Val Asp Pro Leu Ile Asp Lys Trp Ile Glu His Pro Asp Asp
            500                 505                 510

Ser Ala Ile Ser His Trp Leu His Asp Gly Met Pro Pro Gly Gln Thr
            515                 520                 525

-continued

```
Arg Asp Arg Glu Tyr Ile Tyr Pro Thr Ile Tyr Val Tyr Leu Leu Gly
    530                 535                 540

Ala Met Gln Glu Pro Gly His Gly Met Ala Ser Thr Leu Val Gly Leu
545                 550                 555                 560

Phe Ser Arg Pro Glu Gln Leu Glu Glu Val Val Asp Asp Pro Thr Leu
                565                 570                 575

Ile Pro Arg Ala Ile Ala Glu Gly Leu Arg Trp Thr Ser Pro Ile Trp
                580                 585                 590

Ser Ala Thr Ala Arg Ile Ser Thr Lys Pro Val Thr Ile Ala Gly Val
            595                 600                 605

Asp Leu Pro Ala Gly Thr Pro Val Met Leu Ser Tyr Gly Ser Ala Asn
    610                 615                 620

His Asp Thr Gly Lys Tyr Glu Ala Pro Ser Gln Tyr Asp Leu His Arg
625                 630                 635                 640

Pro Pro Leu Pro His Leu Ala Phe Gly Ala Gly Asn His Ala Cys Ala
                645                 650                 655

Gly Ile Tyr Phe Ala Asn His Val Met Arg Ile Ala Leu Glu Glu Leu
                660                 665                 670

Phe Glu Ala Ile Pro Asn Leu Glu Arg Asp Thr Arg Glu Gly Val Glu
            675                 680                 685

Phe Trp Gly Trp Gly Phe Arg Gly Pro Thr Ser Leu His Val Thr Trp
    690                 695                 700

Glu Val
705
```

```
<210> SEQ ID NO 3
<211> LENGTH: 1221
<212> TYPE: DNA
<213> ORGANISM: Amycolatopsis sp. ATCC 39116
<220> FEATURE:
<221> NAME/KEY: CDS
<222> LOCATION: (1)..(1221)

<400> SEQUENCE: 3
```

```
atg acg acg acc gaa cgg ccc gat ctc gcc tgg ctc gac gag gtc acc      48
Met Thr Thr Thr Glu Arg Pro Asp Leu Ala Trp Leu Asp Glu Val Thr
1               5                   10                  15 atg acg cag ctc gag cgc aac ccg tac gag gtg tac gag cgg ctg cgc      96
Met Thr Gln Leu Glu Arg Asn Pro Tyr Glu Val Tyr Glu Arg Leu Arg
            20                  25                  30 gcg gag gcg ccg ctg gcc ttc gtg ccg gtg ctg ggg tcc tac gtc gcc     144
Ala Glu Ala Pro Leu Ala Phe Val Pro Val Leu Gly Ser Tyr Val Ala
        35                  40                  45 tcg acc gcc gag gtc tgc cgc gaa gtc gcg acc agc ccg gac ttc gag     192
Ser Thr Ala Glu Val Cys Arg Glu Val Ala Thr Ser Pro Asp Phe Glu
    50                  55                  60 gcc gtc atc acc ccg gcc ggc cgc acc ttc ggg cac ccg gcg atc         240
Ala Val Ile Thr Pro Ala Gly Arg Thr Phe Gly His Pro Ala Ile
65                  70                  75                  80 atc ggc gtc aac ggc gac atc cac gcc gac ctg cgc tcc atg gtc gag     288
Ile Gly Val Asn Gly Asp Ile His Ala Asp Leu Arg Ser Met Val Glu
                85                  90                  95 ccc gcc ctg cag ccc gcc gag gtg gac cgc tgg atc gac gac ctg gtg     336
Pro Ala Leu Gln Pro Ala Glu Val Asp Arg Trp Ile Asp Asp Leu Val
            100                 105                 110 cgg ccc atc gcg cgc cgc tac ctg gag cgg ttc gaa aac gac ggg cac     384
Arg Pro Ile Ala Arg Arg Tyr Leu Glu Arg Phe Glu Asn Asp Gly His
        115                 120                 125
```

```
gcc gaa ctg gtg gcg cag tac tgc gag ccg gtc agc gtc cgc tcg ctc      432
Ala Glu Leu Val Ala Gln Tyr Cys Glu Pro Val Ser Val Arg Ser Leu
        130                 135                 140 ggc gac ctg ctc ggc ctg cag gag gtc gac tcg gac aag ctg cgc gag      480
Gly Asp Leu Leu Gly Leu Gln Glu Val Asp Ser Asp Lys Leu Arg Glu
145                 150                 155                 160 tgg ttc gcc aag ctg aac cgc tcg ttc acc aac gcc gcc gtc gac gag      528
Trp Phe Ala Lys Leu Asn Arg Ser Phe Thr Asn Ala Ala Val Asp Glu
                165                 170                 175 aac ggc gag ttc gcc aac ccc gag ggc ttc gcc gag ggc gac cag gcg      576
Asn Gly Glu Phe Ala Asn Pro Glu Gly Phe Ala Glu Gly Asp Gln Ala
            180                 185                 190 aag gcc gag atc cgc gcc gtc gtc gac ccg ctg atc gac aag tgg atc      624
Lys Ala Glu Ile Arg Ala Val Val Asp Pro Leu Ile Asp Lys Trp Ile
        195                 200                 205 gag cac ccc gac gac agc gcc att tcg cac tgg ctg cac gac ggc atg      672
Glu His Pro Asp Asp Ser Ala Ile Ser His Trp Leu His Asp Gly Met
210                 215                 220 ccg ccc ggc cag acc cgc gac cgc gag tac atc tac ccg acg atc tac      720
Pro Pro Gly Gln Thr Arg Asp Arg Glu Tyr Ile Tyr Pro Thr Ile Tyr
225                 230                 235                 240 gtg tac ctg ctc ggc gcg atg cag gaa ccc ggc cac ggc atg gcc tcc      768
Val Tyr Leu Leu Gly Ala Met Gln Glu Pro Gly His Gly Met Ala Ser
                245                 250                 255 acc ctg gtc ggc ctg ttc agc agg ccc gag cag ctg gaa gag gtg gtc      816
Thr Leu Val Gly Leu Phe Ser Arg Pro Glu Gln Leu Glu Glu Val Val
            260                 265                 270 gac gac ccc acg ctg atc ccg cgg gcg atc gcc gag ggc ctg cgg tgg      864
Asp Asp Pro Thr Leu Ile Pro Arg Ala Ile Ala Glu Gly Leu Arg Trp
        275                 280                 285 acc tcg ccg atc tgg tcg gcc acc gcc cgc atc tcc acc aag ccg gtg      912
Thr Ser Pro Ile Trp Ser Ala Thr Ala Arg Ile Ser Thr Lys Pro Val
290                 295                 300 acc atc gcc ggg gtc gac ctg ccc gcc ggc acg ccg gtg atg ctc tcc      960
Thr Ile Ala Gly Val Asp Leu Pro Ala Gly Thr Pro Val Met Leu Ser
305                 310                 315                 320 tac ggc tcg gcc aac cac gac acc ggc aag tac gag gcg ccc tcg cag     1008
Tyr Gly Ser Ala Asn His Asp Thr Gly Lys Tyr Glu Ala Pro Ser Gln
                325                 330                 335 tac gac ctg cac cgc ccg ccg ctg ccg cac ctc gcc ttc ggc gcg ggc     1056
Tyr Asp Leu His Arg Pro Pro Leu Pro His Leu Ala Phe Gly Ala Gly
            340                 345                 350 aac cac gcg tgc gcg ggc atc tac ttc gcc aac cac gtc atg cgg atc     1104
Asn His Ala Cys Ala Gly Ile Tyr Phe Ala Asn His Val Met Arg Ile
        355                 360                 365 gcg ctg gag gag ctg ttc gag gcc atc ccg aac ctg gag cgc gac acc     1152
Ala Leu Glu Glu Leu Phe Glu Ala Ile Pro Asn Leu Glu Arg Asp Thr
370                 375                 380 cgc gag ggc gtc gag ttc tgg ggc tgg ggc ttc cgc ggc ccc acc tcg     1200
Arg Glu Gly Val Glu Phe Trp Gly Trp Gly Phe Arg Gly Pro Thr Ser
385                 390                 395                 400 ctg cac gtc acc tgg gag gtg                                         1221
Leu His Val Thr Trp Glu Val
                405

<210> SEQ ID NO 4
<211> LENGTH: 407
<212> TYPE: PRT
<213> ORGANISM: Amycolatopsis sp. ATCC 39116
```

<400> SEQUENCE: 4

```
Met Thr Thr Thr Glu Arg Pro Asp Leu Ala Trp Leu Asp Glu Val Thr
1               5                   10                  15

Met Thr Gln Leu Glu Arg Asn Pro Tyr Glu Val Tyr Glu Arg Leu Arg
            20                  25                  30

Ala Glu Ala Pro Leu Ala Phe Val Pro Val Leu Gly Ser Tyr Val Ala
        35                  40                  45

Ser Thr Ala Glu Val Cys Arg Glu Val Ala Thr Ser Pro Asp Phe Glu
    50                  55                  60

Ala Val Ile Thr Pro Ala Gly Gly Arg Thr Phe Gly His Pro Ala Ile
65                  70                  75                  80

Ile Gly Val Asn Gly Asp Ile His Ala Asp Leu Arg Ser Met Val Glu
                85                  90                  95

Pro Ala Leu Gln Pro Ala Glu Val Asp Arg Trp Ile Asp Asp Leu Val
            100                 105                 110

Arg Pro Ile Ala Arg Arg Tyr Leu Glu Arg Phe Glu Asn Asp Gly His
        115                 120                 125

Ala Glu Leu Val Ala Gln Tyr Cys Glu Pro Val Ser Val Arg Ser Leu
    130                 135                 140

Gly Asp Leu Leu Gly Leu Gln Glu Val Asp Ser Asp Lys Leu Arg Glu
145                 150                 155                 160

Trp Phe Ala Lys Leu Asn Arg Ser Phe Thr Asn Ala Ala Val Asp Glu
                165                 170                 175

Asn Gly Glu Phe Ala Asn Pro Glu Gly Phe Ala Glu Gly Asp Gln Ala
            180                 185                 190

Lys Ala Glu Ile Arg Ala Val Val Asp Pro Leu Ile Asp Lys Trp Ile
        195                 200                 205

Glu His Pro Asp Asp Ser Ala Ile Ser His Trp Leu His Asp Gly Met
    210                 215                 220

Pro Pro Gly Gln Thr Arg Asp Arg Glu Tyr Ile Tyr Pro Thr Ile Tyr
225                 230                 235                 240

Val Tyr Leu Leu Gly Ala Met Gln Glu Pro Gly His Gly Met Ala Ser
                245                 250                 255

Thr Leu Val Gly Leu Phe Ser Arg Pro Glu Gln Leu Glu Glu Val Val
            260                 265                 270

Asp Asp Pro Thr Leu Ile Pro Arg Ala Ile Ala Glu Gly Leu Arg Trp
        275                 280                 285

Thr Ser Pro Ile Trp Ser Ala Thr Ala Arg Ile Ser Thr Lys Pro Val
    290                 295                 300

Thr Ile Ala Gly Val Asp Leu Pro Ala Gly Thr Pro Val Met Leu Ser
305                 310                 315                 320

Tyr Gly Ser Ala Asn His Asp Thr Gly Lys Tyr Glu Ala Pro Ser Gln
                325                 330                 335

Tyr Asp Leu His Arg Pro Pro Leu Pro His Leu Ala Phe Gly Ala Gly
            340                 345                 350

Asn His Ala Cys Ala Gly Ile Tyr Phe Ala Asn His Val Met Arg Ile
        355                 360                 365

Ala Leu Glu Glu Leu Phe Glu Ala Ile Pro Asn Leu Glu Arg Asp Thr
    370                 375                 380

Arg Glu Gly Val Glu Phe Trp Gly Trp Gly Phe Arg Gly Pro Thr Ser
385                 390                 395                 400

Leu His Val Thr Trp Glu Val
                405
```

-continued

```
<210> SEQ ID NO 5
<211> LENGTH: 933
<212> TYPE: DNA
<213> ORGANISM: Acinetobacter baylyi ADP1
<220> FEATURE:
<221> NAME/KEY: CDS
<222> LOCATION: (1)..(933)

<400> SEQUENCE: 5
```

| | | | | | | | | | | | | | | | | |
|---|---|---|---|---|---|---|---|---|---|---|---|---|---|---|---|---|
| atg | gaa | gtt | aaa | ata | ttc | aat | act | cag | gat | gtg | caa | gat | ttt | tta | cgt | 48 |
| Met | Glu | Val | Lys | Ile | Phe | Asn | Thr | Gln | Asp | Val | Gln | Asp | Phe | Leu | Arg | |
| 1 | | | | 5 | | | | | 10 | | | | | 15 | | |
| gtt | gca | agc | gga | ctt | gag | caa | gaa | ggt | ggc | aat | ccg | cgt | gta | aag | cag | 96 |
| Val | Ala | Ser | Gly | Leu | Glu | Gln | Glu | Gly | Gly | Asn | Pro | Arg | Val | Lys | Gln | |
| | | | 20 | | | | | 25 | | | | | 30 | | | |
| atc | atc | cat | cgt | gtg | ctt | tca | gat | tta | tat | aaa | gcc | att | gaa | gat | ttg | 144 |
| Ile | Ile | His | Arg | Val | Leu | Ser | Asp | Leu | Tyr | Lys | Ala | Ile | Glu | Asp | Leu | |
| | 35 | | | | | 40 | | | | | 45 | | | | | |
| aat | atc | act | tca | gat | gaa | tac | tgg | gca | ggt | gtg | gca | tat | tta | aat | cag | 192 |
| Asn | Ile | Thr | Ser | Asp | Glu | Tyr | Trp | Ala | Gly | Val | Ala | Tyr | Leu | Asn | Gln | |
| 50 | | | | | 55 | | | | | 60 | | | | | | |
| cta | ggt | gcc | aat | caa | gaa | gct | ggt | tta | ctc | tcg | cca | ggc | ttg | ggt | ttt | 240 |
| Leu | Gly | Ala | Asn | Gln | Glu | Ala | Gly | Leu | Leu | Ser | Pro | Gly | Leu | Gly | Phe | |
| 65 | | | | | 70 | | | | | 75 | | | | | 80 | |
| gac | cat | tac | ctc | gat | atg | cgt | atg | gat | gcc | gaa | gat | gcc | gca | cta | ggt | 288 |
| Asp | His | Tyr | Leu | Asp | Met | Arg | Met | Asp | Ala | Glu | Asp | Ala | Ala | Leu | Gly | |
| | | | | 85 | | | | | 90 | | | | | 95 | | |
| att | gaa | aat | gcg | aca | cca | cgt | acc | att | gaa | ggc | ccg | cta | tac | gtg | gca | 336 |
| Ile | Glu | Asn | Ala | Thr | Pro | Arg | Thr | Ile | Glu | Gly | Pro | Leu | Tyr | Val | Ala | |
| | | | 100 | | | | | 105 | | | | | 110 | | | |
| ggt | gcg | cct | gaa | tcg | gta | ggt | tat | gcg | cgc | atg | gat | gac | gga | agt | gat | 384 |
| Gly | Ala | Pro | Glu | Ser | Val | Gly | Tyr | Ala | Arg | Met | Asp | Asp | Gly | Ser | Asp | |
| | | 115 | | | | | 120 | | | | | 125 | | | | |
| cca | aat | ggt | cat | acc | ctg | att | cta | cat | ggc | acg | atc | ttt | gat | gca | gat | 432 |
| Pro | Asn | Gly | His | Thr | Leu | Ile | Leu | His | Gly | Thr | Ile | Phe | Asp | Ala | Asp | |
| | 130 | | | | | 135 | | | | | 140 | | | | | |
| gga | aaa | cct | tta | ccc | aat | gcc | aaa | gtt | gaa | atc | tgg | cat | gcc | aat | acc | 480 |
| Gly | Lys | Pro | Leu | Pro | Asn | Ala | Lys | Val | Glu | Ile | Trp | His | Ala | Asn | Thr | |
| 145 | | | | | 150 | | | | | 155 | | | | | 160 | |
| aaa | ggc | ttt | tat | tca | cac | ttc | gac | cca | aca | ggc | gag | cag | cag | gcg | ttc | 528 |
| Lys | Gly | Phe | Tyr | Ser | His | Phe | Asp | Pro | Thr | Gly | Glu | Gln | Gln | Ala | Phe | |
| | | | | 165 | | | | | 170 | | | | | 175 | | |
| aat | atg | cgc | cgt | agt | att | att | acc | gat | gaa | aac | ggt | cag | tat | cgc | gtt | 576 |
| Asn | Met | Arg | Arg | Ser | Ile | Ile | Thr | Asp | Glu | Asn | Gly | Gln | Tyr | Arg | Val | |
| | | | 180 | | | | | 185 | | | | | 190 | | | |
| cgt | acc | att | ttg | cct | gcg | ggt | tat | ggt | tgc | cca | cca | gaa | ggt | cca | acg | 624 |
| Arg | Thr | Ile | Leu | Pro | Ala | Gly | Tyr | Gly | Cys | Pro | Pro | Glu | Gly | Pro | Thr | |
| | | 195 | | | | | 200 | | | | | 205 | | | | |
| caa | cag | ttg | ctg | aat | cag | ttg | ggc | cgt | cat | ggt | aac | cgc | cct | gcg | cac | 672 |
| Gln | Gln | Leu | Leu | Asn | Gln | Leu | Gly | Arg | His | Gly | Asn | Arg | Pro | Ala | His | |
| | 210 | | | | | 215 | | | | | 220 | | | | | |
| att | cac | tat | ttt | gtt | tct | gcc | gat | gga | cac | cgc | aaa | cta | act | acg | caa | 720 |
| Ile | His | Tyr | Phe | Val | Ser | Ala | Asp | Gly | His | Arg | Lys | Leu | Thr | Thr | Gln | |
| 225 | | | | | 230 | | | | | 235 | | | | | 240 | |
| att | aat | gtg | gct | ggc | gat | ccg | tac | acc | tat | gac | gac | ttt | gct | tat | gca | 768 |
| Ile | Asn | Val | Ala | Gly | Asp | Pro | Tyr | Thr | Tyr | Asp | Asp | Phe | Ala | Tyr | Ala | |
| | | | | 245 | | | | | 250 | | | | | 255 | | |
| acc | cgt | gaa | ggc | ttg | gtg | gtt | gat | gca | gtg | gaa | cac | acc | gat | cct | gaa | 816 |
| Thr | Arg | Glu | Gly | Leu | Val | Val | Asp | Ala | Val | Glu | His | Thr | Asp | Pro | Glu | |
| | | | 260 | | | | | 265 | | | | | 270 | | | |

```
gcc att aag gcc aat gat gtt gaa ggc cca ttc gct gaa atg gtt ttc    864
Ala Ile Lys Ala Asn Asp Val Glu Gly Pro Phe Ala Glu Met Val Phe
    275                 280                 285 gat cta aaa ttg acg cgt ttg gtt gat ggt gta gat aac caa gtt gtt    912
Asp Leu Lys Leu Thr Arg Leu Val Asp Gly Val Asp Asn Gln Val Val
290                 295                 300 gat cgt cca cgt cta gcg gtg                                        933
Asp Arg Pro Arg Leu Ala Val
305                 310

<210> SEQ ID NO 6
<211> LENGTH: 311
<212> TYPE: PRT
<213> ORGANISM: Acinetobacter baylyi ADP1

<400> SEQUENCE: 6

Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Pro Gly Leu Gly Phe
65                  70                  75                  80

Asp His Tyr Leu Asp Met Arg Met Asp Ala Glu Asp Ala Ala Leu Gly
                85                  90                  95

Ile Glu Asn Ala Thr Pro Arg Thr Ile Glu Gly Pro Leu Tyr Val Ala
            100                 105                 110

Gly Ala Pro Glu Ser Val Gly Tyr Ala Arg Met Asp Asp Gly Ser Asp
        115                 120                 125

Pro Asn Gly His Thr Leu Ile Leu His Gly Thr Ile Phe Asp Ala Asp
    130                 135                 140

Gly Lys Pro Leu Pro Asn Ala Lys Val Glu Ile Trp His Ala Asn Thr
145                 150                 155                 160

Lys Gly Phe Tyr Ser His Phe Asp Pro Thr Gly Glu Gln Gln Ala Phe
                165                 170                 175

Asn Met Arg Arg Ser Ile Ile Thr Asp Glu Asn Gly Gln Tyr Arg Val
            180                 185                 190

Arg Thr Ile Leu Pro Ala Gly Tyr Gly Cys Pro Pro Glu Gly Pro Thr
        195                 200                 205

Gln Gln Leu Leu Asn Gln Leu Gly Arg His Gly Asn Arg Pro Ala His
    210                 215                 220

Ile His Tyr Phe Val Ser Ala Asp Gly His Arg Lys Leu Thr Thr Gln
225                 230                 235                 240

Ile Asn Val Ala Gly Asp Pro Tyr Thr Tyr Asp Asp Phe Ala Tyr Ala
                245                 250                 255

Thr Arg Glu Gly Leu Val Val Asp Ala Val Glu His Thr Asp Pro Glu
            260                 265                 270

Ala Ile Lys Ala Asn Asp Val Glu Gly Pro Phe Ala Glu Met Val Phe
        275                 280                 285

Asp Leu Lys Leu Thr Arg Leu Val Asp Gly Val Asp Asn Gln Val Val
    290                 295                 300

Asp Arg Pro Arg Leu Ala Val
305                 310
```

```
<210> SEQ ID NO 7
<211> LENGTH: 1002
<212> TYPE: DNA
<213> ORGANISM: Amycolatopsis sp. ATCC 39116
<220> FEATURE:
<221> NAME/KEY: CDS
<222> LOCATION: (1)..(1002)

<400> SEQUENCE: 7
```

| gtg | acg | ttc | gcg | gtc | agc | gtc | ggg | ggc | agg | cgg | gtc | gac | tgc | gag | ccc | 48 |
|---|---|---|---|---|---|---|---|---|---|---|---|---|---|---|---|---|
| Val | Thr | Phe | Ala | Val | Ser | Val | Gly | Gly | Arg | Arg | Val | Asp | Cys | Glu | Pro | |
| 1 | | | | 5 | | | | | 10 | | | | | 15 | | |

| ggc | cag | acc | ctg | ctc | gag | gcg | ttc | ctg | cgc | ggc | ggg | gtg | tgg | atg | ccc | 96 |
|---|---|---|---|---|---|---|---|---|---|---|---|---|---|---|---|---|
| Gly | Gln | Thr | Leu | Leu | Glu | Ala | Phe | Leu | Arg | Gly | Gly | Val | Trp | Met | Pro | |
| | | | 20 | | | | | 25 | | | | | 30 | | | |

| aac | tcg | tgc | aac | cag | ggc | acc | tgc | ggc | acc | tgc | aag | ctc | cag | gtg | ctc | 144 |
|---|---|---|---|---|---|---|---|---|---|---|---|---|---|---|---|---|
| Asn | Ser | Cys | Asn | Gln | Gly | Thr | Cys | Gly | Thr | Cys | Lys | Leu | Gln | Val | Leu | |
| | | 35 | | | | | 40 | | | | | 45 | | | | |

| tcc | ggc | gag | gtc | gac | cac | ggc | ggc | gcc | ccg | gag | gac | acc | ctc | agc | gcc | 192 |
|---|---|---|---|---|---|---|---|---|---|---|---|---|---|---|---|---|
| Ser | Gly | Glu | Val | Asp | His | Gly | Gly | Ala | Pro | Glu | Asp | Thr | Leu | Ser | Ala | |
| | 50 | | | | | 55 | | | | | 60 | | | | | |

| gag | gaa | cgc | gcg | tcc | gga | ctg | gcg | ctc | gcc | tgc | cag | gcc | cgt | ccg | ctc | 240 |
|---|---|---|---|---|---|---|---|---|---|---|---|---|---|---|---|---|
| Glu | Glu | Arg | Ala | Ser | Gly | Leu | Ala | Leu | Ala | Cys | Gln | Ala | Arg | Pro | Leu | |
| 65 | | | | | 70 | | | | | 75 | | | | | 80 | |

| gcc | gac | acg | gag | gtg | cgc | agc | acc | gcc | gac | gcc | ggg | cgc | gtc | acg | cac | 288 |
|---|---|---|---|---|---|---|---|---|---|---|---|---|---|---|---|---|
| Ala | Asp | Thr | Glu | Val | Arg | Ser | Thr | Ala | Asp | Ala | Gly | Arg | Val | Thr | His | |
| | | | | 85 | | | | | 90 | | | | | 95 | | |

| ccg | ctg | cgg | gac | ctg | acg | gcc | acc | gtg | ctg | gag | gtc | gcc | gac | atc | gcg | 336 |
|---|---|---|---|---|---|---|---|---|---|---|---|---|---|---|---|---|
| Pro | Leu | Arg | Asp | Leu | Thr | Ala | Thr | Val | Leu | Glu | Val | Ala | Asp | Ile | Ala | |
| | | | 100 | | | | | 105 | | | | | 110 | | | |

| cgc | gac | acc | cgc | cgg | gtg | ctg | ctg | ggc | ctg | gcc | gag | ccg | ctg | gcg | ttc | 384 |
|---|---|---|---|---|---|---|---|---|---|---|---|---|---|---|---|---|
| Arg | Asp | Thr | Arg | Arg | Val | Leu | Leu | Gly | Leu | Ala | Glu | Pro | Leu | Ala | Phe | |
| | | 115 | | | | | 120 | | | | | 125 | | | | |

| gag | gcc | ggg | cag | tac | gtc | gag | ctg | gtc | gtg | ccc | ggc | tcc | ggc | gcg | cgg | 432 |
|---|---|---|---|---|---|---|---|---|---|---|---|---|---|---|---|---|
| Glu | Ala | Gly | Gln | Tyr | Val | Glu | Leu | Val | Val | Pro | Gly | Ser | Gly | Ala | Arg | |
| | 130 | | | | | 135 | | | | | 140 | | | | | |

| cgg | cag | tac | tcg | ctg | gcc | aac | acg | gcc | gac | gag | gac | aag | gtg | ctg | gag | 480 |
|---|---|---|---|---|---|---|---|---|---|---|---|---|---|---|---|---|
| Arg | Gln | Tyr | Ser | Leu | Ala | Asn | Thr | Ala | Asp | Glu | Asp | Lys | Val | Leu | Glu | |
| 145 | | | | | 150 | | | | | 155 | | | | | 160 | |

| ctg | cac | gtc | cgg | cgc | gtg | ccc | ggt | ggg | gtc | gcc | acc | gac | ggc | tgg | ctc | 528 |
|---|---|---|---|---|---|---|---|---|---|---|---|---|---|---|---|---|
| Leu | His | Val | Arg | Arg | Val | Pro | Gly | Gly | Val | Ala | Thr | Asp | Gly | Trp | Leu | |
| | | | | 165 | | | | | 170 | | | | | 175 | | |

| ttc | gac | ggg | ctc | gcc | gcc | ggc | gac | cgg | gtc | gag | gcg | acc | ggg | ccg | ctc | 576 |
|---|---|---|---|---|---|---|---|---|---|---|---|---|---|---|---|---|
| Phe | Asp | Gly | Leu | Ala | Ala | Gly | Asp | Arg | Val | Glu | Ala | Thr | Gly | Pro | Leu | |
| | | | 180 | | | | | 185 | | | | | 190 | | | |

| ggc | gac | ttc | cac | ctg | ccg | ccg | ccg | gac | gag | gac | gac | ggc | ggc | ccg | atg | 624 |
|---|---|---|---|---|---|---|---|---|---|---|---|---|---|---|---|---|
| Gly | Asp | Phe | His | Leu | Pro | Pro | Pro | Asp | Glu | Asp | Asp | Gly | Gly | Pro | Met | |
| | | 195 | | | | | 200 | | | | | 205 | | | | |

| gtg | ctc | atc | ggc | ggc | gga | acc | ggg | ctg | gcg | ccg | ctg | gtc | ggc | atc | gcc | 672 |
|---|---|---|---|---|---|---|---|---|---|---|---|---|---|---|---|---|
| Val | Leu | Ile | Gly | Gly | Gly | Thr | Gly | Leu | Ala | Pro | Leu | Val | Gly | Ile | Ala | |
| | 210 | | | | | 215 | | | | | 220 | | | | | |

| cgc | acc | gcg | ctg | gcc | cgg | cac | ccg | tcg | cgc | gaa | gtg | ctg | ctg | tac | cac | 720 |
|---|---|---|---|---|---|---|---|---|---|---|---|---|---|---|---|---|
| Arg | Thr | Ala | Leu | Ala | Arg | His | Pro | Ser | Arg | Glu | Val | Leu | Leu | Tyr | His | |
| 225 | | | | | 230 | | | | | 235 | | | | | 240 | |

| ggg | gtg | cgc | ggc | gcg | gcg | gac | ctg | tac | gac | ctc | ggc | cgg | ttc | gcc | gag | 768 |
|---|---|---|---|---|---|---|---|---|---|---|---|---|---|---|---|---|
| Gly | Val | Arg | Gly | Ala | Ala | Asp | Leu | Tyr | Asp | Leu | Gly | Arg | Phe | Ala | Glu | |
| | | | | 245 | | | | | 250 | | | | | 255 | | |

| atc | gcg | gag | gag | cac | ccg | ggt | ttc | cgg | ttc | gtg | ccg | gtg | ctg | tcg | gac | 816 |
|---|---|---|---|---|---|---|---|---|---|---|---|---|---|---|---|---|
| Ile | Ala | Glu | Glu | His | Pro | Gly | Phe | Arg | Phe | Val | Pro | Val | Leu | Ser | Asp | |
| | | | 260 | | | | | 265 | | | | | 270 | | | |

```
gag ccg gat ccg gcg tac cgg ggc ggt ttc ccg acc gac gcg ttc gtc      864
Glu Pro Asp Pro Ala Tyr Arg Gly Gly Phe Pro Thr Asp Ala Phe Val
        275                 280                 285 gag gac gtc ccc agt gga cgc ggc tgg tcc ggc tgg ctg tgc ggc ccg      912
Glu Asp Val Pro Ser Gly Arg Gly Trp Ser Gly Trp Leu Cys Gly Pro
    290                 295                 300 ccg gcg atg gtc gag gcc ggg gtg aag gcg ttc aaa cgg cgg cgc atg      960
Pro Ala Met Val Glu Ala Gly Val Lys Ala Phe Lys Arg Arg Arg Met
305                 310                 315                 320 tcg ccg cgg cgg atc cac cgg gag aag ttc acg ccg gcc tcg              1002
Ser Pro Arg Arg Ile His Arg Glu Lys Phe Thr Pro Ala Ser
                325                 330
```

<210> SEQ ID NO 8
<211> LENGTH: 334
<212> TYPE: PRT
<213> ORGANISM: Amycolatopsis sp. ATCC 39116

<400> SEQUENCE: 8

```
Val Thr Phe Ala Val Ser Val Gly Gly Arg Arg Val Asp Cys Glu Pro
1               5                   10                  15

Gly Gln Thr Leu Leu Glu Ala Phe Leu Arg Gly Gly Val Trp Met Pro
            20                  25                  30

Asn Ser Cys Asn Gln Gly Thr Cys Gly Thr Cys Lys Leu Gln Val Leu
        35                  40                  45

Ser Gly Glu Val Asp His Gly Gly Ala Pro Glu Asp Thr Leu Ser Ala
    50                  55                  60

Glu Glu Arg Ala Ser Gly Leu Ala Leu Ala Cys Gln Ala Arg Pro Leu
65                  70                  75                  80

Ala Asp Thr Glu Val Arg Ser Thr Ala Ala Gly Arg Val Thr His
                85                  90                  95

Pro Leu Arg Asp Leu Thr Ala Thr Val Leu Glu Val Ala Asp Ile Ala
            100                 105                 110

Arg Asp Thr Arg Arg Val Leu Leu Gly Leu Ala Glu Pro Leu Ala Phe
        115                 120                 125

Glu Ala Gly Gln Tyr Val Glu Leu Val Val Pro Gly Ser Gly Ala Arg
    130                 135                 140

Arg Gln Tyr Ser Leu Ala Asn Thr Ala Asp Glu Asp Lys Val Leu Glu
145                 150                 155                 160

Leu His Val Arg Arg Val Pro Gly Gly Val Ala Thr Asp Gly Trp Leu
                165                 170                 175

Phe Asp Gly Leu Ala Ala Gly Asp Arg Val Glu Ala Thr Gly Pro Leu
            180                 185                 190

Gly Asp Phe His Leu Pro Pro Asp Glu Asp Gly Gly Pro Met
        195                 200                 205

Val Leu Ile Gly Gly Thr Gly Leu Ala Pro Leu Val Gly Ile Ala
    210                 215                 220

Arg Thr Ala Leu Ala Arg His Pro Ser Arg Glu Val Leu Leu Tyr His
225                 230                 235                 240

Gly Val Arg Gly Ala Ala Asp Leu Tyr Asp Leu Gly Arg Phe Ala Glu
                245                 250                 255

Ile Ala Glu Glu His Pro Gly Phe Arg Phe Val Pro Val Leu Ser Asp
            260                 265                 270

Glu Pro Asp Pro Ala Tyr Arg Gly Gly Phe Pro Thr Asp Ala Phe Val
        275                 280                 285
```

```
Glu Asp Val Pro Ser Gly Arg Gly Trp Ser Gly Trp Leu Cys Gly Pro
    290             295             300

Pro Ala Met Val Glu Ala Gly Val Lys Ala Phe Lys Arg Arg Arg Met
305             310             315             320

Ser Pro Arg Arg Ile His Arg Glu Lys Phe Thr Pro Ala Ser
            325             330

<210> SEQ ID NO 9
<211> LENGTH: 2244
<212> TYPE: DNA
<213> ORGANISM: Artificial Sequence
<220> FEATURE:
<223> OTHER INFORMATION: Chimeric construct
<220> FEATURE:
<221> NAME/KEY: CDS
<222> LOCATION: (1)..(2244)

<400> SEQUENCE: 9 atg gaa gtt aaa ata ttc aat act cag gat gtg caa gat ttt tta cgt      48
Met Glu Val Lys Ile Phe Asn Thr Gln Asp Val Gln Asp Phe Leu Arg
1               5                   10                  15 gtt gca agc gga ctt gag caa gaa ggt ggc aat ccg cgt gta aag cag      96
Val Ala Ser Gly Leu Glu Gln Glu Gly Gly Asn Pro Arg Val Lys Gln
                20                  25                  30 atc atc cat cgt gtg ctt tca gat tta tat aaa gcc att gaa gat ttg     144
Ile Ile His Arg Val Leu Ser Asp Leu Tyr Lys Ala Ile Glu Asp Leu
            35                  40                  45 aat atc act tca gat gaa tac tgg gca ggt gtg gca tat tta aat cag     192
Asn Ile Thr Ser Asp Glu Tyr Trp Ala Gly Val Ala Tyr Leu Asn Gln
        50                  55                  60 cta ggt gcc aat caa gaa gct ggt tta ctc tcg cca ggc ttg ggt ttt     240
Leu Gly Ala Asn Gln Glu Ala Gly Leu Leu Ser Pro Gly Leu Gly Phe
65                  70                  75                  80 gac cat tac ctc gat atg cgt atg gat gcc gaa gat gcc gca cta ggt     288
Asp His Tyr Leu Asp Met Arg Met Asp Ala Glu Asp Ala Ala Leu Gly
                85                  90                  95 att gaa aat gcg aca cca cgt acc att gaa ggc ccg cta tac gtg gca     336
Ile Glu Asn Ala Thr Pro Arg Thr Ile Glu Gly Pro Leu Tyr Val Ala
            100                 105                 110 ggt gcg cct gaa tcg gta ggt tat gcg cgc atg gat gac gga agt gat     384
Gly Ala Pro Glu Ser Val Gly Tyr Ala Arg Met Asp Asp Gly Ser Asp
        115                 120                 125 cca aat ggt cat acc ctg att cta cat ggc acg atc ttt gat gca gat     432
Pro Asn Gly His Thr Leu Ile Leu His Gly Thr Ile Phe Asp Ala Asp
    130                 135                 140 gga aaa cct tta ccc aat gcc aaa gtt gaa atc tgg cat gcc aat acc     480
Gly Lys Pro Leu Pro Asn Ala Lys Val Glu Ile Trp His Ala Asn Thr
145                 150                 155                 160 aaa ggc ttt tat tca cac ttc gac cca aca ggc gag cag cag gcg ttc     528
Lys Gly Phe Tyr Ser His Phe Asp Pro Thr Gly Glu Gln Gln Ala Phe
                165                 170                 175 aat atg cgc cgt agt att att acc gat gaa aac ggt cag tat cgc gtt     576
Asn Met Arg Arg Ser Ile Ile Thr Asp Glu Asn Gly Gln Tyr Arg Val
            180                 185                 190 cgt acc att ttg cct gcg ggt tat ggt tgc cca cca gaa ggt cca acg     624
Arg Thr Ile Leu Pro Ala Gly Tyr Gly Cys Pro Pro Glu Gly Pro Thr
        195                 200                 205 caa cag ttg ctg aat cag ttg ggc cgt cat ggt aac cgc cct gcg cac     672
Gln Gln Leu Leu Asn Gln Leu Gly Arg His Gly Asn Arg Pro Ala His
    210                 215                 220
```

```
att cac tat ttt gtt tct gcc gat gga cac cgc aaa cta act acg caa        720
Ile His Tyr Phe Val Ser Ala Asp Gly His Arg Lys Leu Thr Thr Gln
225                 230                 235                 240 att aat gtg gct ggc gat ccg tac acc tat gac gac ttt gct tat gca        768
Ile Asn Val Ala Gly Asp Pro Tyr Thr Tyr Asp Asp Phe Ala Tyr Ala
            245                 250                 255 acc cgt gaa ggc ttg gtg gtt gat gca gtg gaa cac acc gat cct gaa        816
Thr Arg Glu Gly Leu Val Val Asp Ala Val Glu His Thr Asp Pro Glu
        260                 265                 270 gcc att aag gcc aat gat gtt gaa ggc cca ttc gct gaa atg gtt ttc        864
Ala Ile Lys Ala Asn Asp Val Glu Gly Pro Phe Ala Glu Met Val Phe
    275                 280                 285 gat cta aaa ttg acg cgt ttg gtt gat ggt gta gat aac caa gtt gtt        912
Asp Leu Lys Leu Thr Arg Leu Val Asp Gly Val Asp Asn Gln Val Val
290                 295                 300 gat cgt cca ctg gca cgc ttg gtt cgt ctg atg cag ttt gct tgt gac        960
Asp Arg Pro Leu Ala Arg Leu Val Arg Leu Met Gln Phe Ala Cys Asp
305                 310                 315                 320 ccc acc att acc gtc att ggt aaa tat aat cat ggt aaa agc cga cta       1008
Pro Thr Ile Thr Val Ile Gly Lys Tyr Asn His Gly Lys Ser Arg Leu
            325                 330                 335 gag agg agg aca gct atg acg acg acc gaa cgg ccc gat ctc gcc tgg       1056
Glu Arg Arg Thr Ala Met Thr Thr Thr Glu Arg Pro Asp Leu Ala Trp
        340                 345                 350 ctc gac gag gtc acc atg acg cag ctc gag cgc aac ccg tac gag gtg       1104
Leu Asp Glu Val Thr Met Thr Gln Leu Glu Arg Asn Pro Tyr Glu Val
    355                 360                 365 tac gag cgg ctg cgc gcg gag gcg ccg ctg gcc ttc gtg ccg gtg ctg       1152
Tyr Glu Arg Leu Arg Ala Glu Ala Pro Leu Ala Phe Val Pro Val Leu
370                 375                 380 ggg tcc tac gtc gcc tcg acc gcc gag gtc tgc cgc gaa gtc gcg acc       1200
Gly Ser Tyr Val Ala Ser Thr Ala Glu Val Cys Arg Glu Val Ala Thr
385                 390                 395                 400 agc ccg gac ttc gag gcc gtc atc acc ccg gcc ggc ggc cgc acc ttc       1248
Ser Pro Asp Phe Glu Ala Val Ile Thr Pro Ala Gly Gly Arg Thr Phe
            405                 410                 415 ggg cac ccg gcg atc atc ggc gtc aac ggc gac atc cac gcc gac ctg       1296
Gly His Pro Ala Ile Ile Gly Val Asn Gly Asp Ile His Ala Asp Leu
        420                 425                 430 cgc tcc atg gtc gag ccc gcc ctg cag ccc gcc gag gtg gac cgc tgg       1344
Arg Ser Met Val Glu Pro Ala Leu Gln Pro Ala Glu Val Asp Arg Trp
    435                 440                 445 atc gac gac ctg gtg cgg ccc atc gcg cgc cgc tac ctg gag cgg ttc       1392
Ile Asp Asp Leu Val Arg Pro Ile Ala Arg Arg Tyr Leu Glu Arg Phe
450                 455                 460 gaa aac gac ggg cac gcc gaa ctg gtg gcg cag tac tgc gag ccg gtc       1440
Glu Asn Asp Gly His Ala Glu Leu Val Ala Gln Tyr Cys Glu Pro Val
465                 470                 475                 480 agc gtc cgc tcg ctc ggc gac ctg ctc ggc ctg cag gag gtc gac tcg       1488
Ser Val Arg Ser Leu Gly Asp Leu Leu Gly Leu Gln Glu Val Asp Ser
            485                 490                 495 gac aag ctg cgc gag tgg ttc gcc aag ctg aac cgc tcg ttc acc aac       1536
Asp Lys Leu Arg Glu Trp Phe Ala Lys Leu Asn Arg Ser Phe Thr Asn
        500                 505                 510 gcc gcc gtc gac gag aac ggc gag ttc gcc aac ccc gag ggc ttc gcc       1584
Ala Ala Val Asp Glu Asn Gly Glu Phe Ala Asn Pro Glu Gly Phe Ala
    515                 520                 525 gag ggc gac cag gcg aag gcc gag atc cgc gcc gtc gtc gac ccg ctg       1632
Glu Gly Asp Gln Ala Lys Ala Glu Ile Arg Ala Val Val Asp Pro Leu
530                 535                 540
```

```
atc gac aag tgg atc gag cac ccc gac gac agc gcc att tcg cac tgg    1680
Ile Asp Lys Trp Ile Glu His Pro Asp Asp Ser Ala Ile Ser His Trp
545                 550                 555                 560 ctg cac gac ggc atg ccg ccc ggc cag acc cgc gac cgc gag tac atc    1728
Leu His Asp Gly Met Pro Pro Gly Gln Thr Arg Asp Arg Glu Tyr Ile
                565                 570                 575 tac ccg acg atc tac gtg tac ctg ctc ggc gcg atg cag gaa ccc ggc    1776
Tyr Pro Thr Ile Tyr Val Tyr Leu Leu Gly Ala Met Gln Glu Pro Gly
            580                 585                 590 cac ggc atg gcc tcc acc ctg gtc ggc ctg ttc agc agg ccc gag cag    1824
His Gly Met Ala Ser Thr Leu Val Gly Leu Phe Ser Arg Pro Glu Gln
        595                 600                 605 ctg gaa gag gtg gtc gac gac ccc acg ctg atc ccg cgg gcg atc gcc    1872
Leu Glu Glu Val Val Asp Asp Pro Thr Leu Ile Pro Arg Ala Ile Ala
    610                 615                 620 gag ggc ctg cgg tgg acc tcg ccg atc tgg tcg gcc acc gcc cgc atc    1920
Glu Gly Leu Arg Trp Thr Ser Pro Ile Trp Ser Ala Thr Ala Arg Ile
625                 630                 635                 640 tcc acc aag ccg gtg acc atc gcc ggg gtc gac ctg ccc gcc ggc acg    1968
Ser Thr Lys Pro Val Thr Ile Ala Gly Val Asp Leu Pro Ala Gly Thr
                645                 650                 655 ccg gtg atg ctc tcc tac ggc tcg gcc aac cac gac acc ggc aag tac    2016
Pro Val Met Leu Ser Tyr Gly Ser Ala Asn His Asp Thr Gly Lys Tyr
            660                 665                 670 gag gcg ccc tcg cag tac gac ctg cac cgc ccg ccg ctg ccg cac ctc    2064
Glu Ala Pro Ser Gln Tyr Asp Leu His Arg Pro Pro Leu Pro His Leu
        675                 680                 685 gcc ttc ggc gcg ggc aac cac gcg tgc gcg ggc atc tac ttc gcc aac    2112
Ala Phe Gly Ala Gly Asn His Ala Cys Ala Gly Ile Tyr Phe Ala Asn
    690                 695                 700 cac gtc atg cgg atc gcg ctg gag gag ctg ttc gag gcc atc ccg aac    2160
His Val Met Arg Ile Ala Leu Glu Glu Leu Phe Glu Ala Ile Pro Asn
705                 710                 715                 720 ctg gag cgc gac acc cgc gag ggc gtc gag ttc tgg ggc tgg ggc ttc    2208
Leu Glu Arg Asp Thr Arg Glu Gly Val Glu Phe Trp Gly Trp Gly Phe
                725                 730                 735 cgc ggc ccc acc tcg ctg cac gtc acc tgg gag gtg                    2244
Arg Gly Pro Thr Ser Leu His Val Thr Trp Glu Val
            740                 745
```

<210> SEQ ID NO 10
<211> LENGTH: 748
<212> TYPE: PRT
<213> ORGANISM: Artificial Sequence
<220> FEATURE:
<223> OTHER INFORMATION: Synthetic Construct

<400> SEQUENCE: 10

```
Met Glu Val Lys Ile Phe Asn Thr Gln Asp Val Gln Asp Phe Leu Arg
1               5                   10                  15

Val Ala Ser Gly Leu Glu Gln Glu Gly Gly Asn Pro Arg Val Lys Gln
            20                  25                  30

Ile Ile His Arg Val Leu Ser Asp Leu Tyr Lys Ala Ile Glu Asp Leu
        35                  40                  45

Asn Ile Thr Ser Asp Glu Tyr Trp Ala Gly Val Ala Tyr Leu Asn Gln
    50                  55                  60

Leu Gly Ala Asn Gln Glu Ala Gly Leu Leu Ser Pro Gly Leu Gly Phe
65                  70                  75                  80

Asp His Tyr Leu Asp Met Arg Met Asp Ala Glu Asp Ala Ala Leu Gly
                85                  90                  95
```

```
Ile Glu Asn Ala Thr Pro Arg Thr Ile Glu Gly Pro Leu Tyr Val Ala
            100                 105                 110
Gly Ala Pro Glu Ser Val Gly Tyr Ala Arg Met Asp Asp Gly Ser Asp
        115                 120                 125
Pro Asn Gly His Thr Leu Ile Leu His Gly Thr Ile Phe Asp Ala Asp
    130                 135                 140
Gly Lys Pro Leu Pro Asn Ala Lys Val Glu Ile Trp His Ala Asn Thr
145                 150                 155                 160
Lys Gly Phe Tyr Ser His Phe Asp Pro Thr Gly Glu Gln Gln Ala Phe
                165                 170                 175
Asn Met Arg Arg Ser Ile Ile Thr Asp Glu Asn Gly Gln Tyr Arg Val
            180                 185                 190
Arg Thr Ile Leu Pro Ala Gly Tyr Gly Cys Pro Pro Glu Gly Pro Thr
        195                 200                 205
Gln Gln Leu Leu Asn Gln Leu Gly Arg His Gly Asn Arg Pro Ala His
    210                 215                 220
Ile His Tyr Phe Val Ser Ala Asp Gly His Arg Lys Leu Thr Thr Gln
225                 230                 235                 240
Ile Asn Val Ala Gly Asp Pro Tyr Thr Tyr Asp Asp Phe Ala Tyr Ala
                245                 250                 255
Thr Arg Glu Gly Leu Val Val Asp Ala Val Glu His Thr Asp Pro Glu
            260                 265                 270
Ala Ile Lys Ala Asn Asp Val Glu Gly Pro Phe Ala Glu Met Val Phe
        275                 280                 285
Asp Leu Lys Leu Thr Arg Leu Val Asp Gly Val Asp Asn Gln Val Val
    290                 295                 300
Asp Arg Pro Leu Ala Arg Leu Val Arg Leu Met Gln Phe Ala Cys Asp
305                 310                 315                 320
Pro Thr Ile Thr Val Ile Gly Lys Tyr Asn His Gly Lys Ser Arg Leu
                325                 330                 335
Glu Arg Arg Thr Ala Met Thr Thr Thr Glu Arg Pro Asp Leu Ala Trp
            340                 345                 350
Leu Asp Glu Val Thr Met Thr Gln Leu Glu Arg Asn Pro Tyr Glu Val
        355                 360                 365
Tyr Glu Arg Leu Arg Ala Glu Ala Pro Leu Ala Phe Val Pro Val Leu
    370                 375                 380
Gly Ser Tyr Val Ala Ser Thr Ala Glu Val Cys Arg Glu Val Ala Thr
385                 390                 395                 400
Ser Pro Asp Phe Glu Ala Val Ile Thr Pro Ala Gly Gly Arg Thr Phe
                405                 410                 415
Gly His Pro Ala Ile Ile Gly Val Asn Gly Asp Ile His Ala Asp Leu
            420                 425                 430
Arg Ser Met Val Glu Pro Ala Leu Gln Pro Ala Glu Val Asp Arg Trp
        435                 440                 445
Ile Asp Asp Leu Val Arg Pro Ile Ala Arg Arg Tyr Leu Glu Arg Phe
    450                 455                 460
Glu Asn Asp Gly His Ala Glu Leu Val Ala Gln Tyr Cys Glu Pro Val
465                 470                 475                 480
Ser Val Arg Ser Leu Gly Asp Leu Leu Gly Leu Gln Glu Val Asp Ser
                485                 490                 495
Asp Lys Leu Arg Glu Trp Phe Ala Lys Leu Asn Arg Ser Phe Thr Asn
            500                 505                 510
```

```
Ala Ala Val Asp Glu Asn Gly Glu Phe Ala Asn Pro Glu Gly Phe Ala
            515                 520                 525

Glu Gly Asp Gln Ala Lys Ala Glu Ile Arg Ala Val Asp Pro Leu
        530                 535                 540

Ile Asp Lys Trp Ile Glu His Pro Asp Ser Ala Ile Ser His Trp
545                 550                 555                 560

Leu His Asp Gly Met Pro Pro Gly Gln Thr Arg Asp Arg Glu Tyr Ile
                565                 570                 575

Tyr Pro Thr Ile Tyr Val Tyr Leu Leu Gly Ala Met Gln Glu Pro Gly
                580                 585                 590

His Gly Met Ala Ser Thr Leu Val Gly Leu Phe Ser Arg Pro Glu Gln
        595                 600                 605

Leu Glu Glu Val Val Asp Asp Pro Thr Leu Ile Pro Arg Ala Ile Ala
    610                 615                 620

Glu Gly Leu Arg Trp Thr Ser Pro Ile Trp Ser Ala Thr Ala Arg Ile
625                 630                 635                 640

Ser Thr Lys Pro Val Thr Ile Ala Gly Val Asp Leu Pro Ala Gly Thr
                645                 650                 655

Pro Val Met Leu Ser Tyr Gly Ser Ala Asn His Asp Thr Gly Lys Tyr
            660                 665                 670

Glu Ala Pro Ser Gln Tyr Asp Leu His Arg Pro Pro Leu Pro His Leu
        675                 680                 685

Ala Phe Gly Ala Gly Asn His Ala Cys Ala Gly Ile Tyr Phe Ala Asn
    690                 695                 700

His Val Met Arg Ile Ala Leu Glu Glu Leu Phe Glu Ala Ile Pro Asn
705                 710                 715                 720

Leu Glu Arg Asp Thr Arg Glu Gly Val Glu Phe Trp Gly Trp Gly Phe
                725                 730                 735

Arg Gly Pro Thr Ser Leu His Val Thr Trp Glu Val
            740                 745
```

<210> SEQ ID NO 11
<211> LENGTH: 1221
<212> TYPE: DNA
<213> ORGANISM: Amycolatopsis sp. ATCC 39116
<220> FEATURE:
<221> NAME/KEY: CDS
<222> LOCATION: (1)..(1221)

<400> SEQUENCE: 11

```
atg acg acg acc gaa cgg ccc gat ctc gcc tgg ctc gac gag gtc acc    48
Met Thr Thr Thr Glu Arg Pro Asp Leu Ala Trp Leu Asp Glu Val Thr
1               5                   10                  15 atg acg cag ctc gag cgc aac ccg tac gag gtg tac gag cgg ctg cgc    96
Met Thr Gln Leu Glu Arg Asn Pro Tyr Glu Val Tyr Glu Arg Leu Arg
            20                  25                  30 gcg gag gcg ccg ctg gcc ttc gtg ccg gtg ctg ggg tcc tac gtc gcc   144
Ala Glu Ala Pro Leu Ala Phe Val Pro Val Leu Gly Ser Tyr Val Ala
        35                  40                  45 tcg acc gcc gag gtc tgc cgc gaa gtc gcg acc agc ccg gac ttc gag   192
Ser Thr Ala Glu Val Cys Arg Glu Val Ala Thr Ser Pro Asp Phe Glu
    50                  55                  60 gcc gtc atc acc ccg gcc ggc gac cgc acc ttc ggg cac ccg gcg atc   240
Ala Val Ile Thr Pro Ala Gly Asp Arg Thr Phe Gly His Pro Ala Ile
65                  70                  75                  80 atc ggc gtc aac ggc gac atc cac gcc gac ctg cgc tcc atg gtc gag   288
Ile Gly Val Asn Gly Asp Ile His Ala Asp Leu Arg Ser Met Val Glu
                85                  90                  95
```

```
ccc gcc ctg cag ccc gcc gag gtg gac cgc tgg atc gac gac ctg gtg         336
Pro Ala Leu Gln Pro Ala Glu Val Asp Arg Trp Ile Asp Asp Leu Val
            100                 105                 110 cgg ccc atc gcg cgc cgc tac ctg gag cgg ttc gaa aac gac ggg cac         384
Arg Pro Ile Ala Arg Arg Tyr Leu Glu Arg Phe Glu Asn Asp Gly His
        115                 120                 125 gcc gaa ctg gtg gcg cag tac tgc gag ccg gtc agc gtc cgc tcg ctc         432
Ala Glu Leu Val Ala Gln Tyr Cys Glu Pro Val Ser Val Arg Ser Leu
    130                 135                 140 ggc gac ctg ctc ggc ctg cag gag gtc gac tcg gac aag ctg cgc gag         480
Gly Asp Leu Leu Gly Leu Gln Glu Val Asp Ser Asp Lys Leu Arg Glu
145                 150                 155                 160 tgg ttc gcc aag ctg aac cgc tcg ttc acc aac gcc gcc gtc gac gag         528
Trp Phe Ala Lys Leu Asn Arg Ser Phe Thr Asn Ala Ala Val Asp Glu
                165                 170                 175 aac ggc gag ttc gcc aac ccc gag ggc ttc gcc gag ggc gac cag gcg         576
Asn Gly Glu Phe Ala Asn Pro Glu Gly Phe Ala Glu Gly Asp Gln Ala
            180                 185                 190 aag gcc gag atc cgc gcc gtc gtc gac ccg ctg atc gac aag tgg atc         624
Lys Ala Glu Ile Arg Ala Val Val Asp Pro Leu Ile Asp Lys Trp Ile
        195                 200                 205 gag cac ccc gac gac agc gcc att tcg cac tgg ctg cac gac ggc atg         672
Glu His Pro Asp Asp Ser Ala Ile Ser His Trp Leu His Asp Gly Met
    210                 215                 220 ccg ccc ggc cag acc cgc gac cgc gag tac atc tac ccg acg atc tac         720
Pro Pro Gly Gln Thr Arg Asp Arg Glu Tyr Ile Tyr Pro Thr Ile Tyr
225                 230                 235                 240 gtg tac ctg ctc ggc gcg atg cag gaa ccc ggc cac ggc atg gcc tcc         768
Val Tyr Leu Leu Gly Ala Met Gln Glu Pro Gly His Gly Met Ala Ser
                245                 250                 255 acc ctg gtc ggc ctg ttc agc agg ccc gag cag ctg gaa gag gtg gtc         816
Thr Leu Val Gly Leu Phe Ser Arg Pro Glu Gln Leu Glu Glu Val Val
            260                 265                 270 gac gac ccc acg ctg atc ccg cgg gcg atc gcc gag ggc ctg cgg tgg         864
Asp Asp Pro Thr Leu Ile Pro Arg Ala Ile Ala Glu Gly Leu Arg Trp
        275                 280                 285 acc tcg ccg atc tgg tcg gcc acc gcc cgc atc tcc acc aag ccg gtg         912
Thr Ser Pro Ile Trp Ser Ala Thr Ala Arg Ile Ser Thr Lys Pro Val
    290                 295                 300 acc atc gcc ggg gtc gac ctg ccc gcc ggc acg ccg gtg atg ctc tcc         960
Thr Ile Ala Gly Val Asp Leu Pro Ala Gly Thr Pro Val Met Leu Ser
305                 310                 315                 320 tac ggc tcg gcc aac cac gac acc ggc aag tac gag gcg ccc tcg cag        1008
Tyr Gly Ser Ala Asn His Asp Thr Gly Lys Tyr Glu Ala Pro Ser Gln
                325                 330                 335 tac gac ctg cac cgc ccg ccg ctg ccg cac ctc gcc ttc ggc gcg ggc        1056
Tyr Asp Leu His Arg Pro Pro Leu Pro His Leu Ala Phe Gly Ala Gly
            340                 345                 350 aac cac gcg tgc gcg ggc atc tac ttc gcc aac cac gtc atg cgg atc        1104
Asn His Ala Cys Ala Gly Ile Tyr Phe Ala Asn His Val Met Arg Ile
        355                 360                 365 gcg ctg gag gag ctg ttc gag gcc atc ccg aac ctg gag cgc gac acc        1152
Ala Leu Glu Glu Leu Phe Glu Ala Ile Pro Asn Leu Glu Arg Asp Thr
    370                 375                 380 cgc gag ggc gtc gag ttc tgg ggc tgg ggc ttc cgc ggc ccc acc tcg        1200
Arg Glu Gly Val Glu Phe Trp Gly Trp Gly Phe Arg Gly Pro Thr Ser
385                 390                 395                 400 ctg cac gtc acc tgg gag gtg                                            1221
Leu His Val Thr Trp Glu Val
                405
```

<210> SEQ ID NO 12
<211> LENGTH: 407
<212> TYPE: PRT
<213> ORGANISM: Amycolatopsis sp. ATCC 39116

<400> SEQUENCE: 12

```
Met Thr Thr Thr Glu Arg Pro Asp Leu Ala Trp Leu Asp Glu Val Thr
1               5                  10                  15

Met Thr Gln Leu Glu Arg Asn Pro Tyr Glu Val Tyr Glu Arg Leu Arg
            20                  25                  30

Ala Glu Ala Pro Leu Ala Phe Val Pro Val Leu Gly Ser Tyr Val Ala
        35                  40                  45

Ser Thr Ala Glu Val Cys Arg Glu Val Ala Thr Ser Pro Asp Phe Glu
    50                  55                  60

Ala Val Ile Thr Pro Ala Gly Asp Arg Thr Phe Gly His Pro Ala Ile
65                  70                  75                  80

Ile Gly Val Asn Gly Asp Ile His Ala Asp Leu Arg Ser Met Val Glu
                85                  90                  95

Pro Ala Leu Gln Pro Ala Glu Val Asp Arg Trp Ile Asp Asp Leu Val
            100                 105                 110

Arg Pro Ile Ala Arg Arg Tyr Leu Glu Arg Phe Glu Asn Asp Gly His
        115                 120                 125

Ala Glu Leu Val Ala Gln Tyr Cys Glu Pro Val Ser Val Arg Ser Leu
    130                 135                 140

Gly Asp Leu Leu Gly Leu Gln Glu Val Asp Ser Asp Lys Leu Arg Glu
145                 150                 155                 160

Trp Phe Ala Lys Leu Asn Arg Ser Phe Thr Asn Ala Ala Val Asp Glu
                165                 170                 175

Asn Gly Glu Phe Ala Asn Pro Glu Gly Phe Ala Glu Gly Asp Gln Ala
            180                 185                 190

Lys Ala Glu Ile Arg Ala Val Val Asp Pro Leu Ile Asp Lys Trp Ile
        195                 200                 205

Glu His Pro Asp Asp Ser Ala Ile Ser His Trp Leu His Asp Gly Met
    210                 215                 220

Pro Pro Gly Gln Thr Arg Asp Arg Glu Tyr Ile Tyr Pro Thr Ile Tyr
225                 230                 235                 240

Val Tyr Leu Leu Gly Ala Met Gln Glu Pro Gly His Gly Met Ala Ser
                245                 250                 255

Thr Leu Val Gly Leu Phe Ser Arg Pro Glu Gln Leu Glu Glu Val Val
            260                 265                 270

Asp Asp Pro Thr Leu Ile Pro Arg Ala Ile Ala Glu Gly Leu Arg Trp
        275                 280                 285

Thr Ser Pro Ile Trp Ser Ala Thr Ala Arg Ile Ser Thr Lys Pro Val
    290                 295                 300

Thr Ile Ala Gly Val Asp Leu Pro Ala Gly Thr Pro Val Met Leu Ser
305                 310                 315                 320

Tyr Gly Ser Ala Asn His Asp Thr Gly Lys Tyr Glu Ala Pro Ser Gln
                325                 330                 335

Tyr Asp Leu His Arg Pro Pro Leu Pro His Leu Ala Phe Gly Ala Gly
            340                 345                 350

Asn His Ala Cys Ala Gly Ile Tyr Phe Ala Asn His Val Met Arg Ile
        355                 360                 365

Ala Leu Glu Glu Leu Phe Glu Ala Ile Pro Asn Leu Glu Arg Asp Thr
    370                 375                 380
```

```
Arg Glu Gly Val Glu Phe Trp Gly Trp Gly Phe Arg Gly Pro Thr Ser
385                 390                 395                 400

Leu His Val Thr Trp Glu Val
                405
```

<210> SEQ ID NO 13
<211> LENGTH: 1002
<212> TYPE: DNA
<213> ORGANISM: Amycolatopsis sp. ATCC 39116
<220> FEATURE:
<221> NAME/KEY: CDS
<222> LOCATION: (1)..(1002)

<400> SEQUENCE: 13

```
gtg acg ttc acg gtc agc gtc ggg ggc agg cgg gtc gac tgc gag ccc      48
Val Thr Phe Thr Val Ser Val Gly Gly Arg Arg Val Asp Cys Glu Pro
1               5                   10                  15 ggc cag acc ctg ctc gag gcg ttc ctg cgc ggg ggg gtg tgg atg ccc      96
Gly Gln Thr Leu Leu Glu Ala Phe Leu Arg Gly Gly Val Trp Met Pro
            20                  25                  30 aac tcg tgc aac cag ggc acc tgc ggc acc tgc aag ctc cag gtg ctc     144
Asn Ser Cys Asn Gln Gly Thr Cys Gly Thr Cys Lys Leu Gln Val Leu
        35                  40                  45 tcc ggc gag gtc gac cac ggc ggc gcc ccg gag gac acc ctc agc gcc     192
Ser Gly Glu Val Asp His Gly Gly Ala Pro Glu Asp Thr Leu Ser Ala
    50                  55                  60 gag gaa cgc gcg tcc gga ctg gcg ctc gcc tgc cag gcc cgt ccg ctc     240
Glu Glu Arg Ala Ser Gly Leu Ala Leu Ala Cys Gln Ala Arg Pro Leu
65                  70                  75                  80 gcc gac acg gag gtg cgc agc acc gcc gac gcc ggg cgc gtc acg cac     288
Ala Asp Thr Glu Val Arg Ser Thr Ala Asp Ala Gly Arg Val Thr His
                85                  90                  95 ccg ctg cgg gac ctg acg gcc acc gtg ctg gag gtc gcc gac atc gcg     336
Pro Leu Arg Asp Leu Thr Ala Thr Val Leu Glu Val Ala Asp Ile Ala
            100                 105                 110 cgc gac acc cgc cgg gtg ctg ctg ggc ctg gcc gag ccg ctg gcg ttc     384
Arg Asp Thr Arg Arg Val Leu Leu Gly Leu Ala Glu Pro Leu Ala Phe
        115                 120                 125 gag gcc ggg cag tac gtc gag ctg gtc gtg ccc ggc tcc ggc gcg cgg     432
Glu Ala Gly Gln Tyr Val Glu Leu Val Val Pro Gly Ser Gly Ala Arg
    130                 135                 140 cgg cag tac tcg ctg gcc aac acg gcc gac gag gac aag gtg ctg gag     480
Arg Gln Tyr Ser Leu Ala Asn Thr Ala Asp Glu Asp Lys Val Leu Glu
145                 150                 155                 160 ctg cac gtc cgg cgc gtg ccc ggt ggg gtc gcc acc gac ggc tgg ctc     528
Leu His Val Arg Arg Val Pro Gly Gly Val Ala Thr Asp Gly Trp Leu
                165                 170                 175 ttc gac ggg ctc gcc gcc ggc gac cgg gtc gag gcg acc ggg ccg ctc     576
Phe Asp Gly Leu Ala Ala Gly Asp Arg Val Glu Ala Thr Gly Pro Leu
            180                 185                 190 ggc gac ttc cac ctg ccg ccg ccg gac gag gac gac ggc ggc ccg atg     624
Gly Asp Phe His Leu Pro Pro Pro Asp Glu Asp Asp Gly Gly Pro Met
        195                 200                 205 gtg ctc atc ggc ggc gga acc ggg ctg gcg ccg ctg gtc ggc atc gcc     672
Val Leu Ile Gly Gly Gly Thr Gly Leu Ala Pro Leu Val Gly Ile Ala
    210                 215                 220 cgc acc gcg ctg gcc cgg cac ccg tcg cgc gaa gtg ctg ctg tac cac     720
Arg Thr Ala Leu Ala Arg His Pro Ser Arg Glu Val Leu Leu Tyr His
225                 230                 235                 240
```

```
ggg gtg cgc ggc gcg gcg gac ctg tac gac ctc ggc cgg ttc gcc gag      768
Gly Val Arg Gly Ala Ala Asp Leu Tyr Asp Leu Gly Arg Phe Ala Glu
            245                 250                 255 atc gcg gag gag cac ccg ggt ttc cgg ttc gtg ccg gtg ctg tcg gac      816
Ile Ala Glu Glu His Pro Gly Phe Arg Phe Val Pro Val Leu Ser Asp
        260                 265                 270 gag ccg gat ccg gcg tac cgg ggc ggt ttc ccg acc gac gcg ttc gtc      864
Glu Pro Asp Pro Ala Tyr Arg Gly Gly Phe Pro Thr Asp Ala Phe Val
    275                 280                 285 gag gac gtc ccc agt gga cgc ggc tgg tcc ggc tgg ctg tgc ggc ccg      912
Glu Asp Val Pro Ser Gly Arg Gly Trp Ser Gly Trp Leu Cys Gly Pro
290                 295                 300 ccg gcg atg gtc gag gcc ggg gtg aag gcg ttc aaa cgg cgg cgc atg      960
Pro Ala Met Val Glu Ala Gly Val Lys Ala Phe Lys Arg Arg Arg Met
305                 310                 315                 320 tcg ccg cgg cgg atc cac cgg gag aag ttc acg ccg gcc tcg              1002
Ser Pro Arg Arg Ile His Arg Glu Lys Phe Thr Pro Ala Ser
                325                 330
```

<210> SEQ ID NO 14
<211> LENGTH: 334
<212> TYPE: PRT
<213> ORGANISM: Amycolatopsis sp. ATCC 39116

<400> SEQUENCE: 14

```
Val Thr Phe Thr Val Ser Val Gly Gly Arg Arg Val Asp Cys Glu Pro
1               5                   10                  15

Gly Gln Thr Leu Leu Glu Ala Phe Leu Arg Gly Gly Val Trp Met Pro
            20                  25                  30

Asn Ser Cys Asn Gln Gly Thr Cys Gly Thr Cys Lys Leu Gln Val Leu
        35                  40                  45

Ser Gly Glu Val Asp His Gly Gly Ala Pro Glu Asp Thr Leu Ser Ala
    50                  55                  60

Glu Glu Arg Ala Ser Gly Leu Ala Leu Ala Cys Gln Ala Arg Pro Leu
65                  70                  75                  80

Ala Asp Thr Glu Val Arg Ser Thr Ala Asp Ala Gly Arg Val Thr His
                85                  90                  95

Pro Leu Arg Asp Leu Thr Ala Thr Val Leu Glu Val Ala Asp Ile Ala
            100                 105                 110

Arg Asp Thr Arg Arg Val Leu Leu Gly Leu Ala Glu Pro Leu Ala Phe
        115                 120                 125

Glu Ala Gly Gln Tyr Val Glu Leu Val Val Pro Gly Ser Gly Ala Arg
    130                 135                 140

Arg Gln Tyr Ser Leu Ala Asn Thr Ala Asp Glu Asp Lys Val Leu Glu
145                 150                 155                 160

Leu His Val Arg Arg Val Pro Gly Gly Val Ala Thr Asp Gly Trp Leu
                165                 170                 175

Phe Asp Gly Leu Ala Ala Gly Asp Arg Val Glu Ala Thr Gly Pro Leu
            180                 185                 190

Gly Asp Phe His Leu Pro Pro Pro Asp Glu Asp Gly Gly Pro Met
        195                 200                 205

Val Leu Ile Gly Gly Gly Thr Gly Leu Ala Pro Leu Val Gly Ile Ala
    210                 215                 220

Arg Thr Ala Leu Ala Arg His Pro Ser Arg Glu Val Leu Leu Tyr His
225                 230                 235                 240

Gly Val Arg Gly Ala Ala Asp Leu Tyr Asp Leu Gly Arg Phe Ala Glu
                245                 250                 255
```

-continued

```
Ile Ala Glu Glu His Pro Gly Phe Arg Phe Val Pro Val Leu Ser Asp
            260                 265                 270

Glu Pro Asp Pro Ala Tyr Arg Gly Gly Phe Pro Thr Asp Ala Phe Val
        275                 280                 285

Glu Asp Val Pro Ser Gly Arg Gly Trp Ser Gly Trp Leu Cys Gly Pro
        290                 295                 300

Pro Ala Met Val Glu Ala Gly Val Lys Ala Phe Lys Arg Arg Arg Met
305                 310                 315                 320

Ser Pro Arg Arg Ile His Arg Glu Lys Phe Thr Pro Ala Ser
                325                 330
```